United States Patent [19]

Maduskuie, Jr.

[11] Patent Number: 5,179,117

[45] Date of Patent: Jan. 12, 1993

[54] ANTIHYPERCHOLESTEROLEMIC 2-SUBSTITUTED IMIDAZOLES

[75] Inventor: Thomas P. Maduskuie, Jr., Wilmington, Del.

[73] Assignee: Du Pont Merck Pharmaceutical Company, Wilmington, Del.

[21] Appl. No.: 811,213

[22] Filed: Dec. 20, 1991

[51] Int. Cl.$^5$ .............. A61K 31/415; C07D 233/70; C07D 233/84; C07D 233/64

[52] U.S. Cl. ................ 514/398; 548/315.1; 548/315.4; 548/315.7; 548/324.1; 548/324.5; 548/323.5; 548/331.5; 548/336.1; 548/338.1; 548/338.5; 548/339.1; 548/341.5; 548/342.1; 548/340.1; 548/342.5; 548/341.1; 548/335.5

[58] Field of Search .............. 548/333, 346, 337, 340, 548/341, 342; 514/398

[56] References Cited

U.S. PATENT DOCUMENTS

| | | | |
|---|---|---|---|
| 3,842,097 | 10/1974 | Tweit | 548/337 |
| 3,915,980 | 10/1975 | Gebert et al. | 548/337 |
| 4,190,666 | 2/1980 | Cherkofsky et al. | 548/337 X |
| 4,228,291 | 10/1980 | Durant et al. | 548/138 |
| 4,269,847 | 5/1981 | Niedballa et al. | 548/337 X |
| 4,413,130 | 11/1983 | White | 548/342 |
| 4,460,598 | 7/1984 | Lautenschlager et al. | 548/337 X |
| 4,623,662 | 11/1986 | DeVries | 514/596 |
| 4,654,358 | 3/1987 | Lautenschlauger et al. | 548/337 X |
| 4,722,927 | 2/1988 | Holmes | 514/256 |
| 4,874,792 | 10/1988 | Gleason et al. | 548/337 X |
| 4,900,744 | 2/1990 | Billheimer et al. | 548/337 X |
| 4,968,713 | 11/1990 | Baldwin et al. | 548/337 X |
| 5,025,015 | 6/1991 | Patoiseau et al. | 548/337 X |
| 5,030,644 | 7/1991 | Baldwin et al. | 548/337 X |

FOREIGN PATENT DOCUMENTS

| | | | |
|---|---|---|---|
| 0372445 | 6/1990 | European Pat. Off. | 548/337 |
| 0437103 | 7/1991 | European Pat. Off. | 548/337 |
| 3323070 | 1/1985 | Fed. Rep. of Germany | 548/337 |
| 3504679 | 8/1986 | Fed. Rep. of Germany | 548/337 |
| 3504680 | 8/1986 | Fed. Rep. of Germany | 548/337 |
| 57-59871 | 4/1982 | Japan | 548/337 |
| 3-24062 | 2/1991 | Japan | 548/337 |

*Primary Examiner*—Floyd D. Higel
*Attorney, Agent, or Firm*—Gildo E. Fato

[57] ABSTRACT

The compounds of the described invention are potent ACAT inhibitors and are useful in pharmaceutical compositions for the treatment of atherosclerosis and have the formulas:

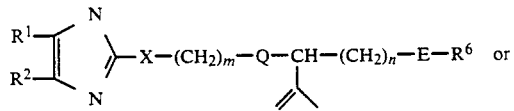

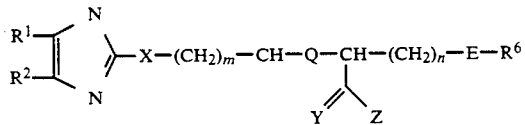

when Q is a double bond wherein:

$R^1$ and $R^2$ are each H, $C_1$-$C_8$alkyl, $C_3$-$C_{10}$cycloalkyl, $C_4$-$C_{10}$-$C_{10}$cyloalkylalkyl, $C_7$-$C_{14}$aralkyl, 2-,3- or 4-pyridinyl, 2-thienyl, 2-furanyl, phenyl optionally substituted by F, Cl, Br, OH, CN, $C_1$-$C_4$ alkoxy, $C_1$-$C_8$alkyl, $CH_3$ $S(O)_r$, $NO_2$, $CF_3$ $NR^7R^8$ or $NR^7C(O)R^8$;

$R^3$ is N.$C_1$-$C_6$alkyl, allyl or benzyl or phenyl both optionally substituted F, Cl, $CH_3$, $CH_3$), or $CF_3$; $C_1$-$C_4$ carboalkyl;

$R^4$ is H, $C_1$-$C_8$alkyl, $C_3$-$C_7$cycloalkyl, $C_4$-$C_{10}$ cycloalkylalkyl, $C_1$-$C_3$ perfluoroalkyl or, benzyl or phenyl both optionally substituted by $C_1$-$C_8$ alkyl, $C_1$-$C_4$-alkoxy, F, Br, Cl, $NH_2$, OH, CN, $CO_2$ H, $CF_3$, $NO_2$, $C_1$-$C_4$ carbalkoxy, $NR^7R^8$ or

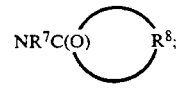

2-,3-, or 4-pyridinyl, pyrimidinyl or biphenyl;

$R^5$ is H, $C_1$-$C_6$ alkyl or benzyl;

$R_6$ is H, $C_1$-$C_8$alkyl, $C_3$-$C_7$ cycloalkyl, $C_4$-$C_{10}$ cycloalkylalkyl or benzyl or phenyl each optionally substituted by $C_{1-4}$alkyl or alkoxy, F, Br, Cl, $NH_2$, OH, CN, $CO_2H$, $CF_3$, $NO_2$, $C_1$-$C_3$ carbarbalkoxy, $NR^7R^8$, $NR^7C(O)^8$; pentafluorophenyl;

$R^7$ and $R^8$ are each H, $C_1$-$C_4$alkyl, benzyl or phenyl;

X is $S(O)_r$, O, $NR^5$, bond;

Y is O, S, $H_2$, $NR^7$;

Z is $NHR^4$, $OR^4$ or $R^4$; provided that when Y is $NR^7$, Z cannot be $OR^4$ or $R^4$;

m,n are 1–6;

r is 0–2;

Q is a single bond, double bond, —C(O)N($R^7$); —N($R^7$)C(O)—, —C(O)O—, —OC(O)—;

E is a single bond, O, $NR^7$, S, —C(O)N($R^7$)—, —N($R^7$)C(O)—, —N($R^7$)C(O)N($R^8$)—, —N($R^7$)-C(O)O—, —OC(O)N($R^7$)—, —N($R^7$) C(NH)N($^8$), —C(O)O—, —OC(O)—;

or a pharmaceutically acceptable salt thereof.

24 Claims, No Drawings

ANTIHYPERCHOLESTEROLEMIC 2-SUBSTITUTED IMIDAZOLES

FIELD OF THE INVENTION

This invention relates to imidazole combinations as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are a limited number of patents in the literature disclosing compounds which are useful as ACAT inhibitors in particular and antiatherosclerotic agents in general. For example, U.S. Pat. No. 4,623,662, issued to De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol.

U.S. Pat. No. 4,460,598, issued to Lautenschläger et al. on Jul. 17, 1984, discloses compounds of the formula:

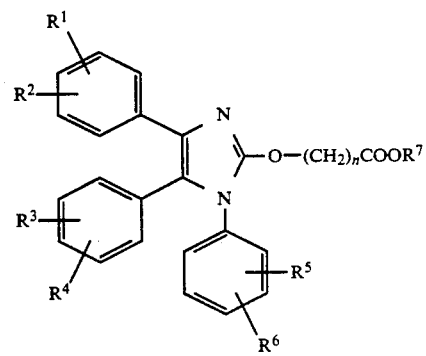

wherein $R^1$, $R^2$, $R^3$, $R^4$, $R^5$ and $R^6$ independently are H, F, Cl, Br, I, alkyl, alkoxy, or $CF_3$, with the proviso that one or several of $R^1$ and $R^2$, $R^3$ and $R^4$, or $R^5$ and $R^6$ taken together represent methylenedioxy;

$R^7$ is H, alkali metal ion, alkyl of 1 to 6 carbon atoms, or benzyl; and n is 0 to 10.

The synthesis and the use of these compounds in the treatment of thromboembolic, inflammatory and/or atherosclerotic diseases is disclosed.

U.S. Pat. No. 4,654,358, issued to Lautenschläger et al. on Mar. 31, 1987, discloses compounds of the formula:

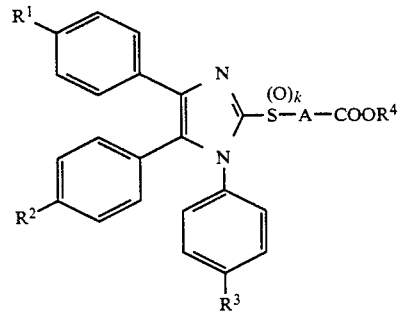

wherein

K is 0, 1, or 2, $R^1$, $R^2$ and $R^3$ independently are H, F, Cl, $CH_3$, $CH_3O$, or $CF^3$;

$R^4$ is H, Na, K, $CH_3$, $CH_3CH_2$, $(CH_3)_2CH$, $CH_3(CH_2)_2$, or butyl;

A is $C(CH_3)_2$, $CH(CH_2)_mCH_3$, $(CH_2)_n$, or $(CH_2)_{n-2}CH(CH_3)$;

m is 0 to 8; and n is 2 to 10.

The synthesis and the use of these compounds in the treatment of inflammatory diseases, diseases of lipid metabolism, and/or hyperlipidemic diseases is disclosed.

German Laid Open Application DE 3504679, Lautenschläger et al., published Aug. 14, 1986, discloses compounds of the formula:

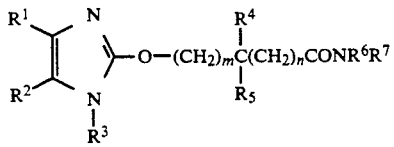

wherein $R^1$, $R^2$ and $R^3$ independently are H, alkyl of 1 to 6 carbon atoms, cycloalkyl of 1 to 6 carbon atoms, or

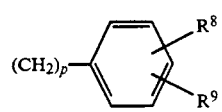

$R^4$ and $R^5$ independently are H, $C_6H_5$, or alkyl of 1 to 9 carbon atoms;

$R^6$ and $R^7$ independently are H, OH, saturated or unsaturated alkyl, cycloalkyl, or hydroxyalkyl of 1 to 10 carbon atoms,

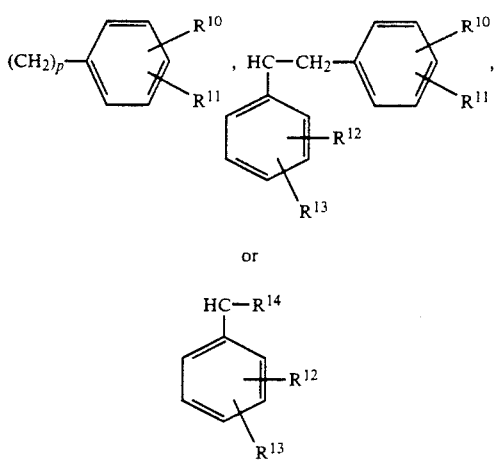

or

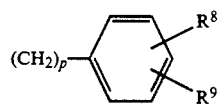

$R^8$, $R^9$, $R^{10}$, $R^{11}$, $R^{12}$ and $R^{13}$ independently are H, F, Cl, Br, $NO_2$, $CH_3CONH$, OH, alkyl of 1 to 3 carbon atoms, $CF_3$, and alkoxy of 1 to 3 carbon atoms, with the proviso that $R^8$ and $R^9$, $R^{10}$ and $R^{11}$, or $R^{12}$ and $R^{13}$ taken together represent methylenedioxy;

$R^{14}$ is alkyl of 1 to 2 carbon atoms;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

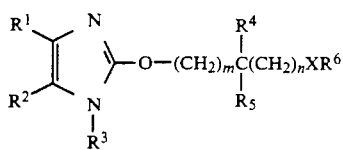

wherein $R^1$, $R^2$ and $R^3$ independently are H, alkyl of 1 to 6 carbons atoms, cycloalkyl of 1 to 6 carbon atoms, or

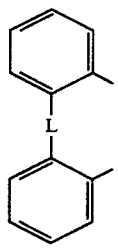

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$, or alkyl of 1 to 9 carbon atoms;

$R^6$ is alkyl, cycloalkyl, hydroxyalkyl of 1 to 20 carbon atoms, H, alkali metal if X is —COO—, 1-phenethyl, or

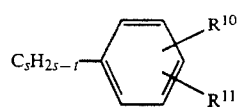

$R^7$ is H, OH if X is —$CONR^7$—, or alkyl of 1 to 4 carbon atoms;

$R^8$, $R^9$, $R^{10}$ and $R^{11}$ are independently H, Cl, F, Br, $NO_2$, $CH_3CONH$, OH, alkyl of 1 to 3 carbon atoms, $CF_3$, or alkoxy of 1 to 3 carbons, or $R^8$ and $R^9$ or $R^{10}$ and $R^{11}$ taken together represent methylene-dioxy;

X is a bond, O, OC(=O)O, C(=O)O, $CONR^7$, OC(=O), or OC(=O)$NR^7$;

m and n taken together represent a whole number from 0 to 9;

p is 0 to 2;

s is 0 to 2; and t is 0 to 2.

The synthesis and the use of these compounds in the treatment of thromboembolic, inflammatory, atherosclerotic, and lipid metabolism diseases in general is disclosed.

Co-pending U.S. patent application Ser. Nos. 07/416,606 filed Oct. 10, 1989 and 07/533,241 filed Jun. 4, 1990, by Wexler et al. discloses compounds of the formula:

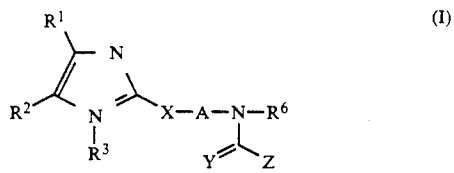

(I)

wherein $R^1$ and $R^2$ are selected independently from H, $C_1$-$C_8$ alkyl, $C_3$-$C_8$ branched alkyl, $C_3$-$C_7$ cycloalkyl, $C_4$-$C_{10}$ cycloalkylalkyl $C_7$-$C_{14}$ araalkyl, 2-, 3- or 4-pyridinyl, 2-thienyl, 2-furanyl, phenyl optionally substituted with 1 to 3 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$; or $R^1$ and $R^2$ can also be taken together as where L is O, $O(CH_2)_{m+1}O$, or $(CH_2)_m$ where M is 0–4;

$R^3$ is H, $C_1$-$C_6$ alkyl, allyl, benzyl, or phenyl optionally substituted with F, Cl, $CH_3$, $CH_3O$, or $CF_3$;

R[4] is straight chain $C_1$-$C_8$ alkyl optionally substituted with F; $C_3$-$C_8$ branched alkyl, $C_3$-$C_7$ cycloalkyl, $C_4$-$C_{10}$ cycloalkylalkyl, $C_7$-$C_{14}$ araalkyl where the aryl group is optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, NR[7]R[8], or NCOR[7]; $C_3$-$C_6$ alkenyl or alkynyl, $C_1$-$C_3$ perfluoroalkyl, phenyl optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, NR[7]R[8] or NCOR[7]; pentafluorophenyl, benzyl optionally substituted with 1 to 3 groups selected from $C_1$-$C_4$ alkyl or alkoxy, F, Br,Cl, $NH_2$, OH, CN, $CO_2H$, $CF_3$, $NO_2$, $C_1$-$C_4$ carboalkoxy, NR[7]R[8], or NCOR[7]; 2-, 3- or 4-pyridinyl, pyrimidinyl, or biphenyl;

R[5] is H, $C_1$-$C_6$ alkyl, or benzyl;

R[6] is $C_1$-$C_8$ alkyl, $C_3$-$C_8$ branched alkyl, $C_3$-$C_7$ cycloalkyl, $C_3$-$C_8$ alkenyl or alkynyl, phenyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, NR[7]R[8], or NCOR[7]; pentafluorophenyl, benzyl optionally substituted with 1 to 3 groups selected from $C_1$-$C_4$ alkyl or alkoxy, F, Br, Cl, $NH_2$, OH CN, $CO_2H$, $CF_3$, $C_1$-$C_4$ carboalkoxy, NR[7]R[8], or NCOR[7];

R[7] and R[8] are selected independently from H or $C_1$-$C_4$ alkyl;

X is $S(O)_r$, O, NR[5], $CH_2$;

A is $C_2$-$C_{10}$ alkyl, $C_3$-$C_{10}$ branched alkyl, $C_3$-$C_{10}$ alkenyl, or $C_3$-$C_{10}$ alkynyl;

Y is O, S, $H_2$, NH;

Z is NHR[4], OR[4], or R[4];

r is 0-2.

The synthesis and the use of these compounds in the treatment of thromboembolic, inflammatory, atherosclerotic, and lipid metabolism diseases in general is disclosed.

Durant et al., U.S. Pat. No. 4,228,291, issued Oct. 14, 1980, teaches compounds of the formula:

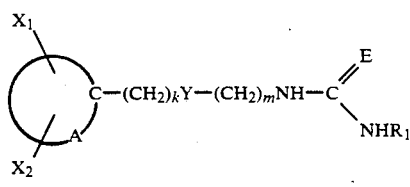

wherein

A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5,6,7,8-tetrahydroimidazol[1,5-a]pyridine ring; $X_1$ is H, lower alkyl, hydroxyl, trifluoromethyl, benzyl, halogen, amino, or

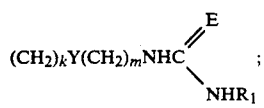

$X_2$ is H, or when $X_1$ is lower alkyl, lower alkyl or halogen; k is 0 to 2 and m is 2 or 3, provided that the sum of k and m is 3 or 4; Y is O, S, or NH; E is NR2; R1 is H, lower alkyl or di-lower alkyl amino-lower alkyl; and R2 is H, nitro, or cyano. The compounds are said to be antihistamines of the $H_2$ receptor blocking type, as well as having anti-inflammatory activity.

White, U.S. Pat. No. 4,413,130, Nov. 1, 1983, discloses histamine $H_2$ receptor antagonists of the formula:

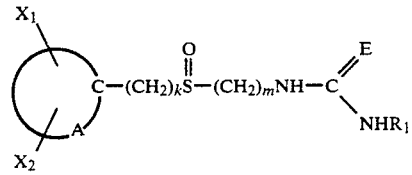

where A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine; $X_1$ and $X_2$ may be H, lower alkyl, trifluoromethyl, hydroxyl, halogen, amino, or $X_1$ and $X_2$ and at least two of the atoms comprising A may form a further ring; k is 0 to 2 and m is 2 or 3, provided that the sum of k and m is 3 or 4; E is O, S, or NR2; R1 is H, lower alkyl, acyl, or dialkylaminoalkyl; and R2 is H, $NO_2$, CN, alkansulphonyl or arenesulphonyl.

There are no known literature references disclosing the compounds of the present invention or suggest that such compounds could be used as ACAT inhibitors or their use to lower cholesterol or in the treatment of atherosclerosis.

SUMMARY OF THE INVENTION

The compounds of the described invention are very potent ACAT inhibitors and are thus expected to be useful in pharmaceutical formulations for the treatment of atherosclerosis. The compounds of this invention should not be construed as limited to any particular antihypercholesterolemic mechanism of action.

The present invention provides novel compounds of Formula (I) and (Ia) processes for their preparations, pharmaceutical compositions containing such heterocyclic compounds, and therapeutic methods for their use as antihypercholesterolemic and or antiatherosclerotic agents.

This invention provides compounds of Formula (I) and (Ia):

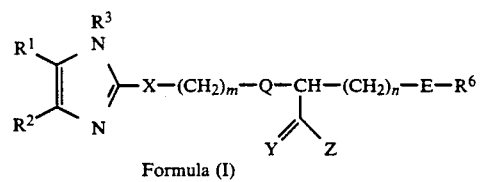

Formula (I)

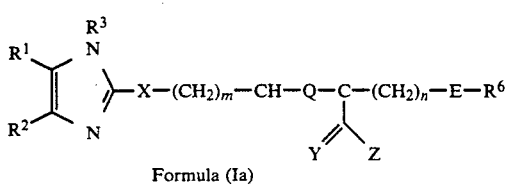

Formula (Ia)

wherein $R^1$ and $R^2$ are selected independently from H, $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl optionally substituted with 1 to 3 groups selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is H, $C_1$-$C_6$ alkyl, allyl, or, benzyl or phenyl both optionally substituted with F, Cl, $CH_3$, $CH_3O$, or $CF_3$; $C_1$-$C_4$ carboalkyl;

$R^4$ is H, straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl or, benzyl or phenyl both optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4-pyridinyl, pyrimidinyl or biphenyl;

$R^5$ is H, $C_1$-$C_6$ alkyl or benzyl;

$R^6$ is H, $C_1$-$C_8$ alkyl, $C_3$-$C_8$ branched alkyl, $C_3$-$C_7$ cycloalkyl, $C_4$-$C_{10}$ cycloalkylalkyl, or benzyl or phenyl both optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_3$ carboalkoxy, $NR^7R^8$, or $NR^7C(O)R^8$; pentafluorophenyl;

$R^7$ and $R^8$ are selected independently from H, or $C_1$-$C_4$ alkyl, benzyl or phenyl;

X is $S(O)_r$, O, $NR^5$, bond;

Y is O, S, $H_2$, $NR^7$;

Z is $NHR^4$, $OR^4$ or $R^4$; provided that when $Y=NR^7$, Z cannot be $OR^4$ or $R^4$;

m and n are 1-6;

r is 0-2;

Q is selected from single bond, double bond, —C(O)N($R^7$)—, —N($R^7$)C(O)—, —C(O)O—, —OC(O)—;

E is selected from a single bond, O, $NR^7$, S, —C(O)N($R^7$)—, —N($R^7$)C(O)—, —N($R^7$)C(O)N($R^8$)—, —N($R^7$)C(O)C(O)O—, —OC(O)N($R^7$)—, —N($R^7$)C(NH)N($R^8$)—, —C(O)O—, —OC(O)—;

or a pharmaceutically acceptable salt thereof.

Preferred are compounds of Formula (I) wherein:

$R^1$ and $R^2$ are selected independently from $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl optionally substituted with 1 to 2 groups selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is H, $C_1$-$C_6$ alkyl, allyl, benzyl, phenyl, or $C_1$-$C_4$ carboalkyl;

$R^4$ is straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl, or, benzyl or phenyl both optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4-pyridinyl, pyrimidinyl or biphenyl;

$R^6$ is $C_1$-$C_8$ alkyl, $C_3$-$C_8$ branched alkyl, $C_3$-$C_7$ cycloalkyl, $C_4$-$C_{10}$ cycloakylalkyl, or, benzyl or phenyl both optionally substituted with 1 to 2 groups selected from $C_1$-$C_4$ alkyl or alkoxy, F, Br, Cl, $NH_2$, OH, CN, $CO_2H$, $CF_3$, $NO_2$, $C_1$-$C_3$ carboalkoxy, $NR^7R^8$, or $NR^7C(O)R^8$; pentafluorophenyl;

$R^7$ and $R^8$ are selected independently from H, C1–C4 alkyl;

X is $S(O)_r$ or bond;

Y is O, S, $H_2$.

More specifically preferred because of their biological activity are compounds of Formula (I) wherein:

$R^1$ and $R^2$ are selected independently from $C_1$-$C_8$ alkyl, $C_3$-$C_8$ branched alkyl, $C_3$-$C_{10}$ cycloalkyl, $C_4$-$C_{10}$ cycloalkylalkyl, $C_7C_{14}$ arylalkyl, 2-, 3-, or 4-pyridinyl, 2-thienyl, 2-furanyl, phenyl optionally substituted with 1 to 2 groups selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ where $R^7$ and $R^8$ are $C_1$-$C_4$ alkyl;

$R^3$ is H, $C_1$-$C_4$ carboalkyl;

$R^4$ is straight chain $C_1$-$C_8$, $C_3$-$C_8$ branched alkyl, $C_3$-$C_7$ cycloalkyl, $C_4$-$C_{10}$ cycloalkylalkyl, or, benzyl or phenyl both optionally substituted with 1 to 2 groups selected from $C_1$-$C_4$ alkyl, $C_3$-$C_6$ branched alkyl, $C_1$-$C_4$ alkoxy, F, Br, Cl, CN, $CF_3$, $NO_2$, $C_1$-$C_4$ carboalkoxy;

$R^6$ is $C_1$-$C_8$ alkyl, $C_3$-$C_8$ branched alkyl, $C_3$-$C_7$ cycloalkyl, $C_4$-$C_{10}$ cycloalkylalkyl, or, phenyl or benzyl both optionally substituted with 1 to 2 groups selected from $C_1$-$C_4$ alkyl or alkoxy, F, Cl, OH, CN, $CF_3$, $NO_2$, $C_1$-$C_3$ carboalkoxy;

$R^7$ and $R^8$ are H;

X is $S(O)_r$;

Y is O, $H_2$.

Specifically preferred are:

N-[4-[4,5-bis(4-methoxyphenyl)-1H-imidazol-2-ylthio]-1-oxobutyl]norleucine, methyl ester N2-[4-[4,5-bis(4-methoxyphenyl)-1H-imidazol-2-ylthio]-1-oxobutyl]-N6-[(phenylmethoxy)-carbonyl]-L-lysine, methyl ester N2-[4-[4,5-bis[4-(dimethylamino)phenyl]-1H-imidazol-2-ylthio]-1-oxobutyl]-N6-[(phenylmethoxy)carbonyl]-L-lysine, methyl ester N6-(1-adamantylcarbonyl)-N2-[4-[4,5-bis(4-methoxyphenyl)-1H-imidazol-2-ylthio]-1-oxobutyl]-L-lysine, methyl ester N2-[4-[4,5-bis(4-methoxyphenyl)-1H-imidazol-2-ylthio]-1-oxobutyl]-N6-[(phenylmethyl)aminocarbonyl]-L-lysine, methyl ester.

DETAILED DESCRIPTION OF THE INVENTION

Synthesis

The novel compounds of Formula (I) may be prepared using the reactions and techniques described in this section. The reactions are performed in solvents appropriate to the reagents and materials employed and suitable for the transformation being effected. It is understood by those skilled in the art of organic synthesis that the functionality present on the imidazole and other portions of the molecule must be compatible with the reagents and reaction conditions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternative methods described must then be used.

It will be appreciated that certain compounds of Formula (I) contain an asymmetrically substituted carbon atom, and may be isolated in optically active or racemic forms. It is well known in the art how to prepare optically active forms, such as by resolution of racemic forms or by synthesis, from optically active starting materials. Also, it is realized that "E" and "Z" stereoisomeric forms of Formula (Ia), when Q is a double bond, are described and may be isolated as a mixture of isomers or as separated stereoisomeric forms. Specific optically active compounds or specific stereoisomers are not implied as to limit this invention unless specifically deemed by the ability to inhibit ACAT enzyme.

The compounds of Formula (I) wherein X is O, S or NH can be prepared by the route shown in Scheme 1.

Formula (4) using amide bond forming reactions which are well known in the chemical literature such as the azide method, mixed carbonic anhydride (isobutylchloroformate) method, carbodiimide (dicyclohexyl carbodiimide, diisopropylcarbodiimide, or water-soluble carbodiimides) method, active ester (p-nitrophenyl ester, N-hydroxysuccinic imide ester) method, carbonyldiimidazole method, or phosphorus reagents such as BOP-Cl. Some of these methods (especially the carbodiimide method) can be enhanced by 1-hydroxybenzotriazole or 4-dimethylaminopyridine. These methods may be used as described in Bodanszky, "Peptide Chemistry: A Practical Textbook", Springer-Verlag, New York (1988); and Bodanszky, et al., "The Practice of Peptide Synthesis", Springer-Verlag, New York (1984).

The compounds of Formula (7) are prepared by con-

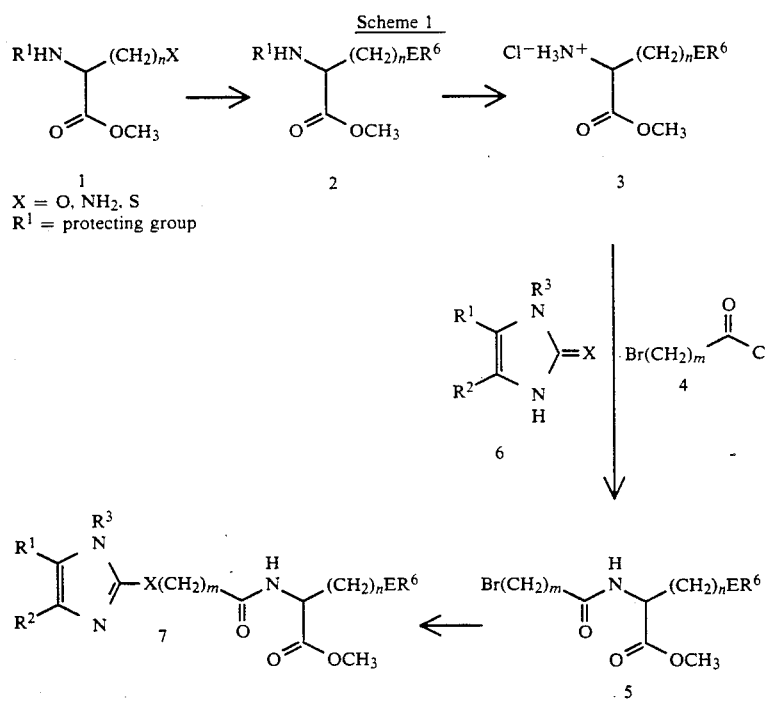

The ester of Formula (2) can be made from an appropriately protected α-amino ester Formula (1) wherein X is O, NH, or S by reaction with the requisite isocyanate, chloroformate, acid chloride, activated urea or activated carboxylic acid derivative, in an appropriate solvent such as hexane, toluene, diethyl ether, methylene chloride or tetrahydrofuran at a temperature at or below the boiling point of the solvent. Alternatively, several compounds of Formula (2) or Formula (3) are available from commercial sources and can be used.

The α-amino compound of Formula (3) can be prepared by deprotection of Formula (2) wherein $R^1$ is t-butoxycarbonyl group, (protecting groups that can be used are listed in T. W. Greene, "Protecting Groups in Organic Synthesis", John Wiley & Sons, New York, 1981), with hydrogen chloride in dioxane, or trifluoroacetic acid, neat, or in methylene chloride. The amides of Formula (5) are prepared by coupling the acid chloride of Formula (4) with the amine of Formula (3) in a solvent such as methylene chloride and an appropriate acid scavenger such as triethylamine. Alternatively, amides of Formula (5) may be prepared by coupling the amine of Formula (3) with an analogous carboxylic acid verting the requisite 4-imidazolin-2-one Formula (6) wherein X is O, or 4-imidazolin-2-thione Formula (6) wherein X is S, into the corresponding alkali metal salt, by addition of a base such as sodium hydride or potassium carbonate and alkylating with a bromide of Formula (5) in a polar solvent such as N,N-dimethylformamide, tetrahydrofuran or acetone. Alternatively, the compound of Formula (7) where X is S or NH may be prepared by direct alkylation of the requisite 4-imidazolin-2-thione Formula (6) wherein X is S or 2-aminoimidazole Formula (6) wherein X is NH with the bromide of Formula (4) without a base in a polar solvent such as N,N-dimethylformamide from ambient temperature to reflux temperature of the solvent.

Compounds of Formula (6) where $R^3$ is H and X is O or NH may sometimes preferentially alkylate the ring nitrogen atom. Therefore, in order to prepare such compounds of Formula (7) wherein X is NH or O it may be necessary to protect the ring nitrogen atom. The protecting group is preferably stable under basic conditions and easily removed under acid conditions e. g., a silyl or trityl group. The protecting group can be removed at any suitable stage in the synthetic sequence for the preparation of the compounds of Formula (1).

The compound of Formula (9), Scheme 2, wherein Z is $OR^4$ or $NHR^4$, as described in the scope of this patent, are prepared by hydrolysis of the methyl ester of Formula (2) to give the corresponding carboxylic acid of Formula (8) by methods which are well known in the chemical literature. For example the hydrolysis can be accomplished by reaction with an alkali metal hydroxide in aqueous and organic solvents such as alcohols, ether, or mixture thereof, followed by acidification. Then the carboxylic acid of Formula (8) can be coupled with the appropriately substituted amine or alcohol as described above in Scheme 1, to give compounds of Formula (9). Compounds of Formula (9) can be used to make compounds of Formula (1) wherein $R^4$ is varied, in analogy to that described in Scheme 1.

The compounds of Formula (1) wherein Z is $R^4$ can be prepared by alkylating an alkali metal salt of an appropriate substituted acetoacetate compound of Formula (10) with a bromide of Formula (11) wherein X is $-C(O)OR^6$ or $-C(O)NHR^6$, or a protected O, NH, or S, as described in Scheme 3. The elaborated acetoacetate of Formula (10) is converted to the alkali metal salt by addition of a base such as sodium hydride, butyl lithium or sodium methoxide in a polar solvent such as N,N-dimethylformamide or tetrahydrofuran at or below ambient temperature.

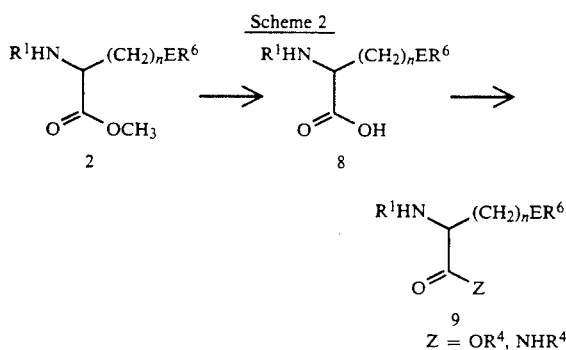

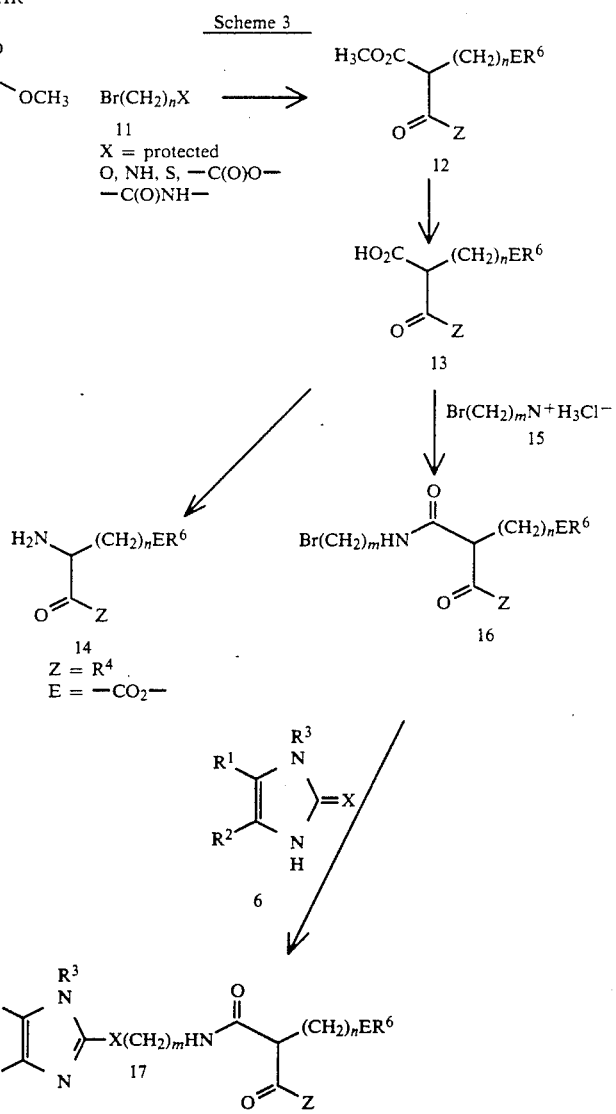

The compound of Formula (13) wherein Z is $R^4$ is prepared by hydrolysis of the carbomethoxy group Formula (12) using an alkali hydroxide as described earlier. The a-amino compound of Formula (14) may be prepared by conversion of the carboxylic acid Formula (13) to it's acyl azide and rearrangement by a Curtius reaction [P. A. S. Smith, Organic Ractions III, 337 (1946)]. The compound of Formula (1) wherein Z=R$^4$ can be made by reaction of compound of Formula (14) as outlined in Scheme 1.

The compound of Formula (1) where Q is —NH—C(O)— can be prepared by coupling a compound of Formula (13) and a bromo amine of Formula (15), by methods previously described, to give compound of Formula (16). This is reacted with the alkali metal salt of the imidazole of Formula (6) to give a compound of Formula (17) by methods previously described.

Alternatively, compounds of Formula (1) can be prepared by converting the imidazole of Formula (6) wherein X is O, S, or NH, and R$^3$ is H or a protecting group as needed, into the corresponding alkali metal salt by addition of a base such as sodium hydride and alkylating with compounds of Formula (18) in a polar aprotic solvent such as N,N-dimethylformamide at an appropriate temperature, Scheme 4.

prepared by methods well known in the literature, Klaus Hoffman, "The Chemistry of Heterocyclic

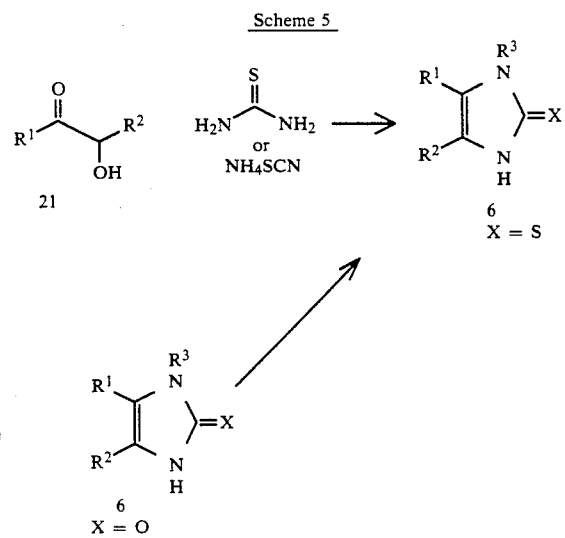

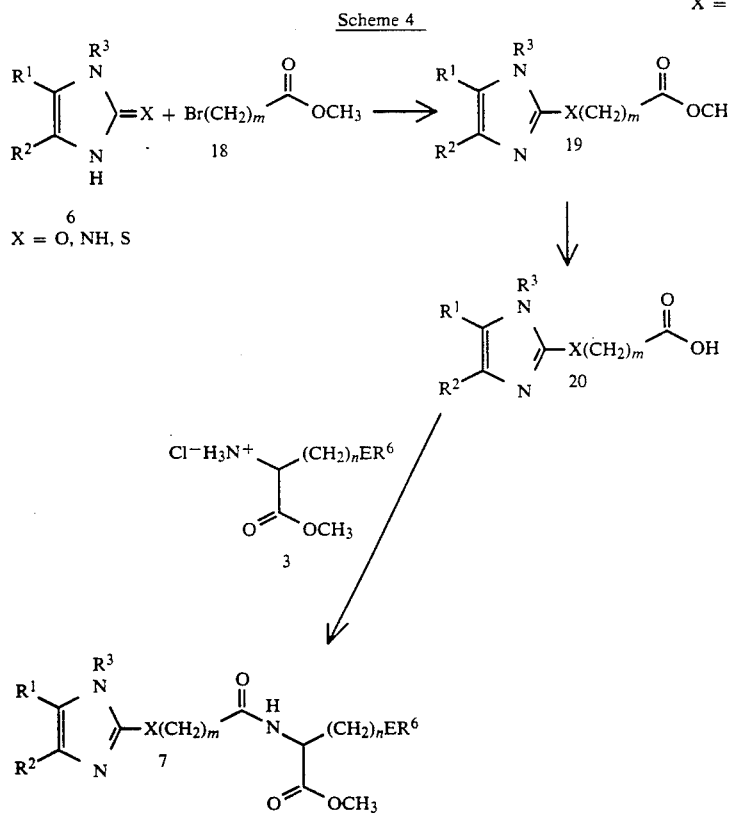

The ester of Formula (19) can be hydrolyzed with a base such as sodium hydroxide or lithium hydroxide in a mixture of water and alcohol and subsequently acidified to give the carboxylic acid of Formula (20). This acid is further converted to compound of Formula (7) by coupling it with an amine of Formula (3) by standard conditions that have been described. Compound of Formula (17) wherein Z is R$^4$ can be prepared by coupling the compound of Formula (20), with a compound of Formula (14) wherein Z is R$^4$, under similar conditions.

The imidazoles of Formula (6), Scheme 5, wherein X is S are available from commercial sources or can be Compounds, Imidazole Part 1, such as by condensing the α-hydroxyketone compounds of Formula (21) with thiourea, ammonium thiocyanate, or an appropriately substituted thiourea in a suitable solvent such as N,N-dimethylformamide, ethanol, or hexanol at a temperature at or below the boiling point of the solvent. Alternatively the compounds of Formula (6) wherein X is S can be prepared from the corresponding 4-imidazolin-2-ones of Formula (6) wherein X is O, (Org Syn Coll., Vol II, 231), by reaction with Lawesson's reagent or diphosphorous pentasulfide in a suitable solvent such as Chem., 28, 46 (1985)), to give the bromo aldehyde of Formula (24).

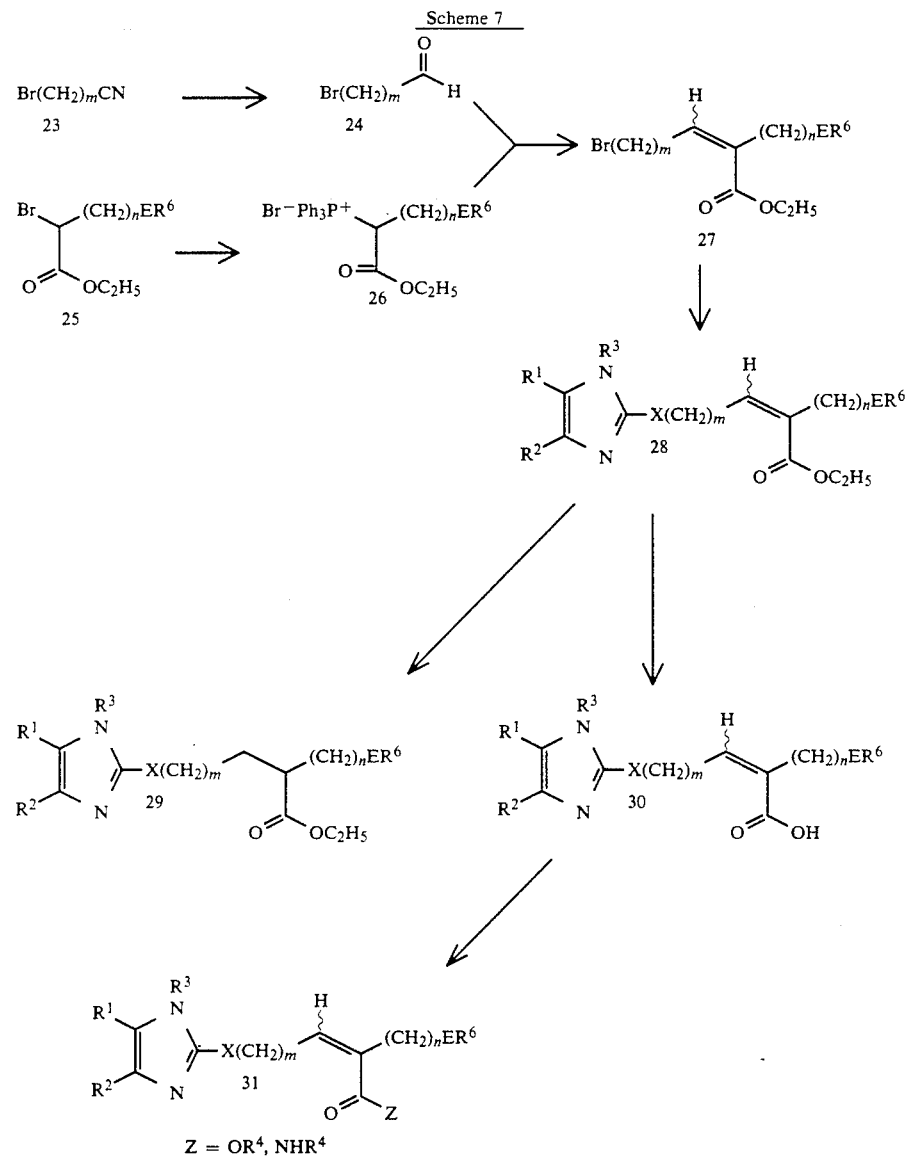

toluene.

The 2-aminoimidazole of Formula (6) wherein X is N can be prepared by the reaction of the appropriately substituted α-amino ketone of Formula (22) with cyanamide Scheme 6.

Scheme 6

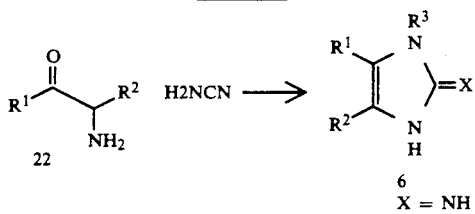

X = NH

The compounds of Formula (1a) wherein Q is a bond or double bond are prepared as described in Scheme 7, starting with reduction of the bromo nitrile of Formula (23) with Raney Nickel (Baker, J., Little, T., J. Med The phosphonium ylid derived from Formula (26) can be generated by the action of a base such as sodium hydride or butyl lithium in a polar solvent such as tetrahydrofuran on the phosphonium salt of Formula (26), and condensed with the aldehyde of Formula (24) to give the compound of Formula (27), as a mixture of "E" and "Z" isomers. The compound of Formula (28) is prepared by alkylating the alkali metal salt of Formula (6) wherein X is S with the bromide of Formula (27) under standard conditions. The double bond may be reduced by a variety of methods well known in the literature for reducing double bond compounds, (P. N. Rylander, Hydrogenation Methods, Acedemic Press, 1985), such as atmospheric catalytic reduction over platinum oxide using hydrogen or ammonium formate or catalytic reduction in a Parr apparatus at elevated hydrogen pressure over palladium on charcoal, in an appropriate solvent such as methanol or ethanol to give the compound of Formula (29).

The compounds of Formula (31) wherein Z is OR[4] or NHR[4] are prepared by hydrolysis of the ester of Formula (28) by methods already described and subsequently coupling the carboxylic acid of Formula (30) with an appropriately substituted alcohol or amine by already elaborated methods.

Preparation of pharmaceutically suitable salts of Formula (I) can be carried out in accordance with well known techniques for forming salts. Physiologically acceptable salts include acid addition salts, e.g., hydrochloric, sulfuric, acetic, trifluoroacetic, succinic, citric, and benzene sulfonic acid salts (*Remington's Pharmaceutical Sciences*, 16th edition, 1980).

The compounds of this invention and their preparation can be further understood by the following examples, which exemplify but do not constitute a limitation of the invention. In these examples, unless otherwise indicated, all temperatures are in degrees centigrade and parts and percentages are by weight.

EXPERIMENTAL

Example 1

Preparation of
N2-[4-[4,5-bis(4-methoxyphenyl)-1H-imidazol-2-ylthio]-1-oxobutyl]-N6-[(phenylmethoxy)carbonyl]-L-lysine, methyl ester Part A 4-Bromobutyryl chloride (1.53 g, 0.00825 mol) was added to a stirred solution of N$^\epsilon$-carbobenzoxy-L-lysine, methyl ester hydrochloride (2.73 g, 0.00825 mol), methylene chloride (30 ml) and 1N sodium hydroxide (16.5 ml) under a nitrogen atmosphere. The reaction mixture was stirred for 2 hours, poured into water (100 ml) and extracted with methylene chloride (2×50 ml). The combined extracts were washed with water, brine, dried over magnesium sulfate and concentrated to give a viscous colorless oil. The crude product was purified by flash chromatography on silica gel (300 ml) eluting hexane: ethyl acetate (50:50) to give N2-[(4-bromo)-1-oxobutyl]-N6-[(phenylmethoxy)carbonyl-L-lysine, methyl ester (3.3 g, 0.0074 mol, 90% yield) as a viscous oil. $^1$H NMR (CDCl$_3$)$\delta$7.35(m, 5H), 6.24(d, 1H), 5.1(s, 2H), 4.90(m, 1H), 4.60-4.50(m, 1H), 3.74(s, 3H), 3.47-3.43(t, 2H), 3.22-3.16(m, 2H), 2.43-2.39(m, 2H), 1.86-1.34(m, 6H).

Part B

A mixture of 4,5-[bis-(4-methoxyphenyl)-1H-imidazol]-2-thione (1.6 g, 0.00519 mol), N2-[(4-bromo)-1-oxobutyl]-N6-[(phenylmethoxy)carbonyl-L-lysine, methyl ester (2.3 g, 0.00519 mol) and potassium carbonate (2.1 g, 0.0155 mol) in N,N-dimethylformamide (15 ml) and tetrahydrofuran (30 ml) was heated to 65° under a nitrogen atmosphere. After 1 hour the reaction was allowed to cool to ambient temperature, filtered and partitioned between ethyl acetate and water. The organic layer was washed with brine, dried over magnesium sulfate and concentrated to give a viscous yellow oil. The product was purified by flash chromatography on silica gel (300 ml) eluting methylene chloride: ethyl acetate (50:50) to give N2-[4-[4,5-bis(4-methoxyphenyl)-1H-imidazol-2-ylthio]-1-oxobutyl]-N6-[(phenylmethoxy)carbonyl]-L-lysine, methyl ester (1.75 g, 0.00259 mol 50% yield) as a white foam, mp 58°-62°, [$\alpha$]D=+7.92(c=0.404, CHCl$_3$). $^1$H NMR (DMSO-d$_6$) $\delta$8.25(d, 1h), 7.38-7.22(m, 10H), 6.9(d, 4H), 4.99(s, 2H), 4.18-4.16(m, 1H), 3.75(s, 6H), 3.59(s, 3H), 3.08-3.03(t, 2H), 2.99-2.93(m, 2H), 2.31-2.26(t, 2H), 1.89-1.84(m, 2H), 1.64-1.23(m, 6H).

Example 2

Preparation of
N2-[4-[4,5-bis(4-methoxyphenyl)-1H-imidazol-2-ylthio]-1-oxobutyl]-L-lysine, methyl ester hydrobromide The N2-[4-[4,5-bis(4-methoxyphenyl)-1H-imidazol-2-ylthio]-1-oxobutyl]-N6-[(phenylmethoxy)carbonyl]-L-lysine, methyl ester (1.60 g, 0.0023 mol) was dissolved in hydrogen bromide 30 wt. % solution in acetic acid (20 ml) under a nitrogen atmosphere at ambient temperature. The reaction mixture was stirred for 1 hour, and diluted with ethyl ether to precipitate a gum. This residue was triturated with ethyl ether to give the title compound (1.58 g, 0.00224 mol, 95% yield) as an off white powder, mp 165°-70°. $^1$H NMR (DMSO-d$_6$) $\delta$8.38 (d, 1H), 7.80-7.70(bs, 3H), 7.39(d, 4H), 7.03(d, 4H), 4.26-4.23(m, 1H), 3.79(s, 6H), 3.6(s, 3H), 3.30-3.26(t, 2H), 2.79-2.73(m, 2H), 2.36-2.31(t, 2H), 1.93-1.86(m, 2H), 1.70-1.31(m, 6H).

Example 3

Preparation of
N6-(1-adamantylcarbonyl)-N2-[4-[4,5-bis(4-methoxyphenyl)-1H-imidazol-2-ylthio]-1-oxobutyl]-L-lysine, methyl ester A solution of 1-adamantanecarbonyl chloride (0.159 g, 0.000804 mol) in methylene chloride (2 ml) was added to a mixture of N2-[4-[4,5-bis(4-methoxyphenyl)-1H-imidazol-2-ylthio]-1-oxobutyl]-L-lysine, methyl ester hydrobromide (0.5 g, 0.000804 mol), triethyl amine (0.24 g, 0.0024 mol) and methylene chloride (20 ml) at ambient temperature under a nitrogen atmosphere. The reaction mixture was stirred for 2 hours, poured into water and extracted with ethyl acetate. The combined organic layer was washed with saturated aqueous ammonium chloride, water, brine, dried over magnesium sulfate and concentrated to give a foam. The foam was purified by flash chromatography on silica gel (50 ml) eluting ethyl acetate to give the title compound (0.4 g, 0.00057 mol, 71% yield) as a white foam, mp 98°-104°. $^1$H NMR (DMSO-d$_6$) $\delta$8.22(d, 1H), 7.35-7.25(m, 5H), 6.87(d, 4H), 4.2-4.12(m, 1H), 3.75(s, 6H), 3.57(s, 3H), 3.1-2.93(m, 4H), 2.27(t, 2H), 1.97-1.5(m, 19H), 1.37-1.17(m, 4H).

Example 4

Preparation of
N2-[4-[4,5-bis(4-methoxyphenyl)-1H-imidazol-2-ylthio]-1-oxobutyl]-N6-[(phenylmethyl)-aminocarbonyl]-L-lysine, methyl ester Employing the method of Example 3, but using benzyl isocyanate, the title compound was isolated as a white foam, mp 80°-85°, (0.475 g, 0.000705 mol, 75% yield). $^1$H NMR (CDCl$_3$) $\delta$7.5-7.0(m, 10H), 6.87(d, 4H), 5.47(t, 1H), 5.07(t, 1H), 4.42-4.37(m, 3H), 3.87(s, 6H), 3.62(s, 3H), 3.15-2.78(m, 4H), 2.45-2.22(m, 2H), 2.01-1.56(m, 4H), 1.37-1.2(m, 4H).

Example 5

Preparation of N6-acetyl-N2-[4-[1-acetyl-4,5-bis(4-methoxyphenyl)-1H-imidazol-2-ylthio]-1-oxobutyl]-L-lysine, methyl ester Employing the method of Example 3, but using acetyl chloride, the title compound was isolated as a foam, mp 52°–56°, (0.11 g, 0.000189 mol 20% yield). $^1$H NMR (CDCl$_3$) δ7.35(d, 2H), 6.97(d, 2H), 6.73(d, 2H), 6.3(d, 1H), 5.75–5.65(m, 1H), 4.63–4.52(m, 1H), 3.87(s, 3H), 3.75(s, 3H), 3.72(s, 3H), 3.37–3.30(m, 2H), 3.17–3.12(m, 2H), 2.47(t, 2H), 2.25–2.17(m, 2H), 1.92(s, 3H), 1.90(s, 3H), 1.85–1.25(m, 6H).

Example 6

Preparation of N6-acetyl-N2-[4-[4,5-bis(4-methoxyphenyl)-1H-imidazol-2-ylthio]-1-oxobutyl]-L-lysine, methyl ester Employing the method of Example 3, but using acetyl chloride, the title compound was isolated as a foam, mp 64°–67°, (0.25 g, 0.000429 mol, 45% yield). $^1$H NMR (CDCl$_3$) δ7.41(bd, 4H), 6.81(d, 4H), 5.85(t, 1H), 4.52–4.42(m, 1H), 3.8(s, 6H), 3.66(s, 3H), 3.25–2.96(m, 4H), 2.57–2.37(m, 2H), 2.11–2.0(m, 2H), 1.92(s, 3H), 1.85–1.25(m, 6H).

Example 7

Preparation of phenylmethyl, (S)-[5-[[4-[4,5-bis(4-methoxyphenyl)-1H-imidazol-2-ylthio]-1-oxobutyl]amino]-6-[(1-methylethyl)amino]-6-oxohexyl]carbamate

Part A

A reaction mixture containing (N$^α$-t-butoxycarbonyl-N$^ε$-carbobenzoxy-L-lysine) (2.6 g, 0.007 mol), isopropylamine (1.22 g, 0.021 mol), 1-(3-dimethylaminopropyl)-3-ethyl carbodiimide hydrochloride (2.0 g, 0.010 mol), 4-dimethylaminopyridine (1.0 g, 0.008 mol) and methylene chloride (50 ml) was stirred under a nitrogen atmosphere at ambient temperature for 24 hours. The reaction was poured into 1N hydrochloric acid and extracted with ethyl acetate. The combined organic layer was washed with 1N hydrochloric acid, water, brine, dried over magnesium sulfate and concentrated to give an oil. The product was purified by flash chromatography on silica gel (300 ml) eluting hexane:ethyl acetate (60:40) to give phenylmethyl 5-(t-butoxycarbonyl)amino-6-(methylethyl)amino-6-oxohexyl]-carbamate (2.3 g, 0.0054 mol, 78% yield) as a colorless oil. $^1$H NMR (CDCl$_3$) δ7.33(s, 5H), 6.0(bd, 1H), 5.25–4.82(m, 4H), 4.12–3.87(m, 2H), 3.24–3.07(m, 2H), 1.87–1.27(m, 15H), 1.17–1.05(d, 6H).

Part B 3M hydrogen chloride in 1,4 dioxane (30 ml) was added to a solution of phenylmethyl 5-(t-butoxycarbonyl)amino-6-(methylethyl)amino-6-oxohexyl]carbamate (3.0 g, 0.0073 mol) and 1,4 dioxane (15 ml) under a nitrogen atmosphere at ambient temperature. After stirring for 2 hours the reaction was concentrated to give phenylmethyl, 5-amino-6-(methylethyl)amino-6-oxohexyl-carbamate, hydrochloride (1.4 g, 0.00039 mol, 54% yield) as a solid, mp 77°–80°. 1H NMR (DMSO-d6) 8.4(d, 1H), 8.25–8.15(bs, 3H), 7.37–7.22(m, 6H), 4.97(s, 2H), 3.90–3.80(m, 1H), 3.62(t, 1H), 3.0–2.92(m, 2H), 1.75–1.62(m, 2H), 1.45–1.20(m, 4H), 1.12–1.02(m, 6H).

Part C

The 4-bromobutyryl chloride (0.703 g, 0.0038 mol) was added to a solution of phenylmethyl, 5-amino-6-(methylethyl)amino-6-oxohexylcarbamate, hydrochloride (1.3 g, 0.0038 mol), triethylamine (1.15 g, 0.0114 mol) and methylene chloride (50 ml) under nitrogen atmosphere at ambient temperature. After stirring for 2 hours, the reaction was poured into 1N hydrochloric acid and extracted with ethyl acetate. The combined organic layer was washed with water, brine, dried over magnesium sulfate and concentrated to give a viscous oil. The product was purified by flash chromatography on silica gel (250 ml) eluting methylene chloride:ethyl acetate (70:30) to give phenylmethyl, [5-[(4-bromo-1-oxobutyl)amino]-6-[(methylethyl)amino]-6-oxohexyl]-carbamate (1.45 g, 0.0031 mol, 81% yield) as a crystalline solid. $^1$H NMR (CDCl$_3$) δ 7.35–7.25(m, 5H), 6.41(bd, 1H), 6.05(bd, 1H), 5.07(s, 2H), 4.95–4.85(m. 1H), 4.35–4.27(m, 1H), 4.1–3.95(m, 1H), 3.42(t, 2H), 3.22–3.12(m, 2H), 2.37(t, 2H), 2.2–2.12(m, 2H), 1.87–1.27(m, 6H), 1.12(d, 6H).

Part D

Employing the method of Example 1, Part B, but using phenylmethyl, [5-[(4-bromo-1-oxobutyl)amino]-6-[(methylethyl)amino]-6-oxohexyl]carbamate and using tetrahydrofuran and N,N-dimethylformamide as solvent, the title compound (0.47 g, 0.000669 mol, 45% yield) was isolated as a foam, mp 85°–88°. $^1$H NMR (DMSO-d$_6$) δ12.37(s, 1H), 7.9(d, 1H), 7.25(d, 1H), 7.4–7.16(m, 10H), 6.91(d, 2H), 6.8(d, 2H), 4.97(s, 2H), 4.2–4.07(m, 1H), 3.8–3.7(m, 1H), 3.76(s, 3H), 3.72(s, 3H), 3.02(t, 2H), 2.97–2.88(m, 2H), 2.27(t, 2H), 1.9–1.8(m, 2H), 1.58–1.12(m, 6H), 1.05–0.95(m, 6H).

Example 8

Preparation of N2-[4-[4,5-bis[4-(dimethylamino)phenyl]-1H-imidazol-2-ylthio]-1-oxobutyl]-N6-[(phenylmethoxy)carbonyl]-L-lysine, methylester Employing the method of Example 1, Part B, but using 4,5-[bis-[4-(dimethylamino)phenyl]-1H-imidazol]-2-thione, the title compound was isolated (0.67 g, 0.000956 mol, 53% yield) as a yellow foam, mp 90°–94°. $^1$H NMR (CDCl$_3$) δ7.72–7.62(m, 1H), 7.42–7.22(m, 9H), 6.57(bd, 4H), 5.3(t, 1H), 5.02(s, 2H), 4.42–4.33(m, 1H), 3.62(s, 3H), 3.17–2.77(m, 16H), 2.65–2.45(m, 2H), 2.00–1.90(m, 2H), 1.81–1.72(m, 2H), 1.5–1.32(m, 4H).

Example 9

Preparation of N-[4-[4,5-bis(4-methoxyphenyl)-1H-imidazol-2-ylthio]-1-oxobutyl]-norleucine, methyl ester

Part A

Employing the method of Example 1, Part A, but using (D,L)-norleucine methyl ester hydrochloride, the N-(4-bromo-1-oxobutyl)norleucine, methyl ester was isolated (0.38 g, 0.00129 mol, 47% yield), as a yellow oil. $^1$H NMR (CDCl$_3$) δ6.06(bd, 1H), 4.62–4.55(m, 1H), 3.77(s, 3H), 3.48(t, 2H), 2.43(t, 2H), 2.25–2.16(m, 2H), 1.91–1.60(m, 2H), 1.37–1.22(m, 4H), 0.9(t, 3H).

Part B

Employing the method of Example 1, Part B, but using the N-(4-bromo-1-oxobutyl)-norleucine, methyl ester the title compound was isolated as a glass (0.21 g, 0.000399 mol, 30% yield). $^1$H NMR (CDCl$_3$) δ7.45(bd, 4H), 6.85(d, 4H), 6.37(d, 1H), 4.6–4.52(m, 1H), 3.80(s, 6H), 3.70(s, 3H), 3.05–2.95(m, 2H), 2.50–2.42(m, 2H), 2.12–2.04(m, 2H), 1.82–1.55(m, 2H), 1.35–1.22(m, 2H), 0.85(t, 3H).

Example 10

Preparation of ethyl, 7-(4,5-diphenyl-1H-imidazol-2-ylthio)-2-pentyl-2-heptenoate Part A The ethyl 2-(triphenylphosphonium) heptanoate, bromide (1.5 g, 0.003 mol) dissolved in tetrahydrofuran (10 ml) was added to a suspension of sodium hydride (washed free of mineral oil) (0.072 g, 0.003 mol) in tetrahydrofuran (50 ml) under a nitrogen atmosphere at ambient temperature. The reaction mixture was stirred for 2 hours, then the 5-bromo-1-pentanal (Baker, J., Little, T., J. Med Chem. 28, 46 (1985), (0.50 g, 0.003 mol) was added and the reaction was heated to reflux for 24 hours. This was allowed to cool to ambient temperature, poured into water and extracted with ethyl acetate. The combined organic layer was washed with water, brine, dried over magnesium sulfate and concentrated to give a solid residue. The product was purified by flash chromatography on silica gel (100 ml) eluting hexane: ethyl acetate (95:5) to give the ethyl, 7-bromo-2-pentyl-2-heptenoate (0.49 g, 0.0016 mol, 54% yield) as a colorless oil. $^1$H NMR (CDCl$_3$) δ6.67(t, 1H), 4.2–4.11(m, 2H), 3.40(t, 2H), 2.32–2.15(m, 4H), 1.95–1.85(m, 2H), 1.65–1.55(m, 2H), 1.42–1.25(m, 9H), 0.9(t, 3H).

Part B

The 4,5-diphenyl-1H-imidazol-2-thione (0.42 g, 0.00162 mol) was added to a suspension of sodium hydride (80%, washed free of mineral oil) (0.039 g, 0.00164 mol) in N,N-dimethylformamide (15 ml) cooled in an ice bath under a nitrogen atmosphere. The reaction mixture stirred for 1 hour and the ethyl, 7-bromo-2-pentyl-2-heptenoate (0.5 g, 0.00164 mol) dissolved in N,N-dimethylformamide (3 ml) was added slowly. This stirred for 1 hour at 0°, then 1 hour at ambient temperature then was poured into water and extracted with ethyl acetate (2×100 ml). The combined organic layer was washed with water, brine, dried over magnesium sulfate and concentrated to give a crude oil. The product was purified by flash chromatography on silica gel eluting hexane: ethyl acetate (85:15) to give ethyl, 7-(4,5-diphenyl-1H-imidazol-2-ylthio)-2-pentyl-2-heptenoate (0.42 g, 0.0008 mol, 54% yield) as a viscous colorless oil. $^1$H NMR (CDCl$_3$) δ9.58–9.53(bs, 1H), 7.62–7.18(m, 10H), 6.7(t, 1H), 4.18–4.08(m, 2H), 3.10(t, 2H), 2.31–2.16(m, 4H), 1.79–1.69(m, 2H), 1.62–1.52(m, 2H), 1.38–1.20(m, 9H), 0.86(t, 3H).

Example 11

Preparation of 7-(4,5-diphenyl-1H-imidazol-2-ylthio)-2-pentyl-2-heptenoic acid

Ethyl, 7-(4,5-diphenyl-1H-imidazol-2-ylthio)-2-pentyl-2-heptenoate (0.37 g, 0.00078 mol) was combined with methanol (5 ml), tetrahydrofuran (2 ml) and lithium hydroxide monohydrate (0.16 g, 0.0038 mol) dissolved in water (3 ml), under a nitrogen atmosphere at ambient temperature. The reaction was heated to 50° for 4 hours, allowed to cool, concentrated then partitioned between ethyl acetate and saturated aqueous ammonium chloride. The organic layer was washed with water, brine, dried over magnesium sulfate and concentrated to give an oil. The product was purified by flash chromatography eluting toluene: ethyl acetate: acetic acid (80:20:2) to give the title compound (0.22 g, 0.00049 mol, 63% yield) as a white foam. $^1$H NMR (CDCl$_3$) δ7.5–7.4(d, 4H), 7.32–7.17(m, 7H), 6.77(t, 1H), 3.08(t, 2H), 2.3–2.15(m, 4H), 1.76–1.68(m, 2H), 1.57–1.50(m, 2H), 1.4–1.2(m, 6H), 0.87(t, 3H).

Example 12

Preparation of N-(2,4-difluorophenyl)-7-(4,5-diphenyl-1H-imidazol-2-ylthio-2-pentyl-2-heptenamide The 7-(4,5-diphenyl-1H-imidazol-2-ylthio)-2-pentyl-2-heptenoic acid (0.14 g, 0.000312 mol), 2,4-difluoroaniline (0.04 g, 0.000312 mol), 1-(3-dimethylaminopropyl)-3-ethyl carbodiimide hydrochloride (0.111 g, 0.000374 mol) and 4-dimethylaminopyridine (0.046 g, 0.000374 mol) were combined in methylene chloride (3 ml) under a nitrogen atmosphere at ambient temperature. The mixture stirred for 48 hours was poured into water and extracted with ethyl acetate. The combined organic layer was washed with water, brine, dried over magnesium sulfate and concentrated to give a yellow oil. The product was purified by flash chromatography on silica gel (100 ml) eluting hexane: isopropanol (95:5) to give the title compound (0.075 g, 0.000134 mol, 43% yield) as a colorless oil. $^1$H NMR (CDCl$_3$) δ9.75–9.3(bs, 1H), 8.25–8.15(m, 1H), 7.65–7.15(m, 11H), 6.9–6.8(m, 2H), 6.37(t, 1H), 3.12(t, 2H), 2.35(t, 2H), 2.27–2.20(m, 2H), 1.85–1.57(m, 4H), 1.48–1.25(m, 6H), 0.87(t, 3H).

Additional compounds, which are listed in Table 1, were prepared or could be prepared analogously according to the procedures listed above.

With the proper selection of reactants, one skilled in the art utilizing the procedures described in examples 1–12 above, may prepare the compounds of examples 1–68 shown in Table 1 below:

TABLE 1

Formula (I)

Formula (Ia) when Q is a double bond

| Ex | R¹ | R² | R³ | X | m | Q | n | E | R⁶ | Y | Z | mp °C. |
|---|---|---|---|---|---|---|---|---|---|---|---|---|
| 1 | p-CH₃OC₆H₄ | p-CH₃OC₆H₄ | H | S | 3 | C(O)NH | 4 | NHC(O)O | CH₂C₆H₅ | O | OCH₃ | 58-62 |
| 2 | p-CH₃OC₆H₄ | p-CH₃OC₆H₄ | H | S | 3 | C(O)NH | 4 | NH | H | O | OCH₃ | 165-70 |
| 3 | p-CH₃OC₆H₄ | p-CH₃OC₆H₄ | H | S | 3 | C(O)NH | 4 | NHC(O) | C(O)C₁₀H₁₅ | O | OCH₃ | 98-104 |
| 4 | p-CH₃OC₆H₄ | p-CH₃OC₆H₄ | C(O)CH₃ | S | 3 | C(O)NH | 4 | NHC(O)NH | CH₂C₆H₅ | O | OCH₃ | 80-85 |
| 5 | p-CH₃OC₆H₄ | p-CH₃OC₆H₄ | H | S | 3 | C(O)NH | 4 | NHC(O) | CH₃ | O | OCH₃ | 52-56 |
| 6 | p-CH₃OC₆H₄ | p-CH₃OC₆H₄ | H | S | 3 | C(O)NH | 4 | NHC(O)O | CH₃ | O | OCH₃ | 64-67 |
| 7 | p-CH₃OC₆H₄ | p-CH₃OC₆H₄ | H | S | 3 | C(O)NH | 4 | NHC(O)O | CH₂C₆H₅ | O | NHCH(CH₃)₂ | 85-88 |
| 8 | p-(CH₃)₂NC₆H₄ | p-CH₃OC₆H₄ | H | S | 3 | C(O)NH | 4 | NHC(O)O | CH₂C₆H₅ | O | OCH₃ | 90-94 |
| 9 | p-CH₃OC₆H₄ | C₆H₅ | H | S | 3 | C(O)NH | 3 | sb | CH₃ | O | OCH₂CH₃ | nmr* |
| 10 | C₆H₅ | C₆H₅ | H | S | 4 | db | 4 | sb | CH₃ | O | OH | nmr* |
| 11 | C₆H₅ | C₆H₅ | H | S | 4 | db | 4 | sb | CH₃ | O | NH2,4-F₂C₆H₃ | nmr* |
| 12 | C₆H₅ | C₆H₅ | H | S | 3 | C(O)NH | 4 | NHC(O)O | CH₂C₆H₅ | O | OCH₃ | nmr* |
| 13 | CH₃ | CH₃ | H | S | 3 | C(O)NH | 4 | O | CH₃ | O | OC₄H₉ | |
| 14 | CH₃ | CH₃ | H | SO | 2 | C(O)O | 4 | NH | p-CH₃OC₆H₄ | S | NHC₆H₅ | |
| 15 | CH₃ | CH₃ | CH₂C₆H₅ | S | 5 | C(O)N(CH₃) | 4 | OC(O)NH | CH₃ | H2 | C₃F₇ | |
| 16 | CH₃ | CH₃ | H | S | 3 | C(O)NH | 4 | NHC(O)O | CH₂C₆H₅ | O | m-ClC₆H₄ | |
| 17 | C₄H₉ | CH₃ | CH₃ | S | 3 | C(O)NH | 3 | C(O)NH | C₆H₅ | O | OCH₃ | |
| 18 | C₄H₉ | CH₃ | H | S | 3 | C(O)O | 3 | C(O)NH | (CH₃)₂CH | O | C₆H₅ | |
| 19 | C₄H₉ | C₄H₉ | C(O)CH₃ | S | 1 | NHC(O) | 2 | C(O)NH | p-CH₃OC(O)C₆H₅ | H2 | p-CH₃OC₆H₄ | |
| 20 | C₄H₉ | C₄H₉ | CH₃ | S | 3 | C(O)O | 4 | OC(O) | p-CH₃OC(O)C₆H₅ | O | NCH₃ | |
| 21 | C₄H₉ | C₄H₉ | H | S | 2 | C(O)O | 4 | N(C₂H₅)C(O) | p-CNC₆H₅ | S | m-CH₃C₆H₄ | |
| 22 | C₆H₅ | C₆H₅ | CH₃ | sb | 5 | C(O)NH | 3 | NHC(O)O | CH₂C₆H₅ | O | OCH₃ | |
| 23 | C₆H₅ | C₆H₅ | CH₃ | SO₂ | 4 | C(O)N(CH₃) | 2 | S | CH₃ | O | OCH₂C₆H₅ | |
| 24 | C₆H₅ | C₆H₅ | H | sb | 2 | N(CH₃)C(O) | 4 | C(O)O | C₆H₁₁ | S | NH2,4-F₂C₆H₃ | |
| 25 | C₆H₅ | C₆H₅ | C(O)CH₃ | S | 4 | NHC(O) | 4 | NHC(O)O | p-NO₂C₆H₄ | O | (CH₃)₃CH | |
| 26 | C₆H₅CH₂ | C₆H₅CH₂ | H | S | 3 | C(O)NH | 4 | C(O)O | CH₂C₆H₅ | O | OCH₃ | |
| 27 | C₆H₅CH₂ | C₆H₅CH₂ | C(O)CH₃ | S | 2 | OC(O) | 5 | C(O)NH | C₆H₁₁ | O | C₆H₅ | |
| 28 | C₆H₁₁ | C₆H₁₁ | H | SO₂ | 5 | C(O)N(CH₃) | 3 | NHC(O)O | C₆H₁₁ | O | OCH(CH₃)₂ | |
| 29 | C₆H₁₁ | C₆H₁₁ | C(O)CH₃ | S | 2 | OC(O) | 3 | C(O)NH | 2,4-F₂C₆H₃ | O | NHC₆H₅ | |
| 30 | C₆H₁₁ | C₆H₁₁ | CH₃ | S | 3 | C(O)NH | 2 | NHC(O)O | CH₂C₆H₅ | O | OCH₃ | |
| 31 | C₆H₁₁ | C₆H₁₁ | C(O)CH₃ | SO | 4 | C(O)O | 4 | C(O)O | C₆H₅ | H2 | NHC₆H₅ | |
| 32 | C₆H₅ | C₆H₅ | CH₃ | S | 3 | C(O)NH | 4 | OC(O)NH | CH₂C₆H₅ | O | CH₂C₆H₅ | |
| 33 | (CH₃)₂CH | (CH₃)₂CH | CH₃ | S | 3 | C(O)NH | 4 | NHC(O)O | CH₂C₆H₅ | O | C₆H₅ | |
| 34 | (CH₃)₂CH | (CH₃)₂CH | C(O)CH₃ | S | 4 | OC(O) | 3 | OC(O)NH | C₆H₁₁ | O | NHC₆H₅ | |
| 35 | (CH₃)₂CH | (CH₃)₂CH | H | sb | 5 | C(O)N(CH₃) | 5 | C(O)NH | C₄H₉ | S | O(o-CH₃C₆H₅) | |
| 36 | p-CH₃SC₆H₄ | p-CH₃SC₆H₄ | CH₃ | S | 3 | C(O)NH | 4 | NHC(O)O | CH₂C₆H₅ | O | OCH₃ | |
| 37 | p-CH₃SC₆H₄ | p-CH₃SC₆H₄ | C(O)CH₃ | S | 3 | N(CH₃)C(O)O | 2 | C(O) | (CH₃)₂CH | O | CH₃C₆H₅ | |
| 38 | p-CH₃SC₆H₄ | p-CH₃SC₆H₄ | CH₃ | S | 3 | OC(O) | 3 | NHC(NH)NH | CH₃ | O | C₄H₉ | |
| 39 | p-CH₃C₆H₄ | p-CH₃C₆H₄ | CH₂C₆H₅ | S | 4 | C(O)NH | 4 | N(C₂H₅)C(O)NH | CH₂C₆H₅ | O | NHC₆H₅ | |
| 40 | p-CH₃C₆H₄ | p-CH₃C₆H₄ | H | S | 4 | NHC(O) | 3 | N(C₂H₅)C(O)NH | C₆H₅ | O | O(p-CO₂HC₆H₄ | |
| 41 | p-CH₃C₆H₄ | p-CH₃C₆H₄ | H | SO₂ | 3 | sb | 4 | O | p-CH₃OC₆H₅ | O | NCH(CH₃)₂ | |
| 42 | p-(CH₃)₂NC₆H₄ | p-(CH₃)₂NC₆H₄ | H | S | 3 | C(O)NH | 4 | NHC(O)NH | p-CH₃OC₆H₅ | O | OCH₃ | |

TABLE 1-continued

Formula (I)

Formula (Ia) when Q is a double bond

| Ex | R¹ | R² | R³ | X | m | Q | n | E | R⁶ | Y | Z | mp °C. |
|---|---|---|---|---|---|---|---|---|---|---|---|---|
| 43 | p-(CH3)2NC6H4 | p-(CH3)2NC6H4 | CH2C6H5 | S | 2 | C(O)NH | 3 | O | CH3 | S | OC4H9 | |
| 44 | p-(CH3)2NC6H4 | p-(CH3)2NC6H4 | H | S0 | 5 | sb | 2 | NH | C6H11 | H2 | NHC6H5 | |
| 45 | p-(CH3)2NC6H4 | p-(CH3)2NC6H4 | CH3 | S | 3 | C(O)O | 4 | OC(O)NH | P-CH3OC6H4 | O | C3F7 | |
| 46 | p-(CH3)2NC6H4 | p-(CH3)2NC6H4 | H | S | 1 | C(O)N(CH3) | 4 | NHC(O)NH | CH3 | O | m-ClC6H4 | |
| 47 | o-CH3C6H4 | o-CH3C6H4 | H | S | 3 | C(O)NH | 4 | NHC(O)O | CH2C6H5 | O | OCH3 | |
| 48 | o-CH3C6H4 | o-CH3C6H4 | C(O)CH3 | S | 3 | NHC(O) | 3 | NH | C6H5 | O | C6H5 | |
| 49 | o-CH3C6H4 | o-CH3C6H4 | H | S | 2 | C(O)O | 2 | C(O)NH | (CH3)2CH | H2 | p-CH3OC6H4 | |
| 50 | o-CH3C6H4 | o-CH3C6H4 | CH3 | S | 3 | C(O)NH | 4 | C(O) | p-CH3OC(O)C6H5 | O | NCH3 | |
| 51 | o-CH3C6H4 | o-CH3C6H4 | H | S | 5 | C(O)NH | 3 | OC(O) | p-CNC6H5 | S | m-CH3C6H4 | |
| 52 | m-CNC6H4 | m-CNC6H4 | H | S | 5 | C(O)NH | 4 | NHC(O)O | CH2C6H5 | O | OCH3 | |
| 53 | m-CNC6H4 | m-CNC6H4 | CH3 | SO2 | 3 | sb | 2 | S | CH3 | O | OCH2C6H5 | |
| 54 | m-CNC6H4 | m-CNC6H4 | H | sb | 4 | C(O)N(CH3) | 4 | C(O)O | C6H11 | S | NH2,4-F2C6H3 | |
| 55 | 4-Pyridindyl | 4-Pyridindyl | C(O)CH3 | S | 5 | N(CH3)C(O) | 2 | NHC(O)O | p-NO2C6H4 | O | (CH3)3CH | |
| 56 | 4-Pyridindyl | 4-Pyridindyl | H | S | 3 | C(O)NH | 4 | NHC(O)0 | CH2C6H5 | O | OCH3 | |
| 57 | 4-Pyridindyl | 4-Pyridindyl | C(O)CH3 | SO2 | 5 | NHC(O) | 3 | C(O)O | C6H11 | O | NHC6H5 | |
| 58 | 4-Pyridindyl | C6H5 | H | S | 3 | OC(O) | 3 | C(O)NH | 2,4-F2C6H3 | O | OCH(CH3)2 | |
| 59 | CH3 | C6H5CH2 | H | S | 3 | C(O)NH | 4 | NHC(O)O | CH2C6H5 | O | OCH3 | |
| 60 | C4H9 | (CH3)2CH | H | S | 3 | C(O)NH | 4 | NHC(O)O | CH2C6H5 | O | OCH3 | |
| 61 | C6H11 | p-CNC6H4 | H | S | 3 | C(O)NH | 4 | NHC(O)O | CH2C6H5 | O | OCH3 | |
| 62 | p-CH3OC6H4 | C6H5 | H | S | 3 | C(O)NH | 4 | NHC(O)O | CH2C6H5 | O | OCH3 | |
| 63 | p-(CH3)2NC6H4 | C4H9 | H | S | 3 | C(O)NH | 4 | NHC(O)O | CH2C6H5 | O | OCH3 | |
| 64 | p-CH3OC6H4 | (CH3)2CH | H | S | 3 | C(O)NH | 4 | NHC(O)O | CH2C6H5 | O | OCH3 | |
| 65 | p-(CH3)2NC6H4 | m-(CH3)2NC6H4 | H | S | 3 | C(O)NH | 4 | NHC(O)O | CH2C6H5 | O | OCH3 | |
| 66 | p-CH3OC6H5 | p-CH3OC6H4 | H | S | 3 | C(O)NH | 4 | NHC(O)O | CH2C6H5 | O | OCH3 | |
| 67 | p-CH3SC6H4 | p-CH3OC6H4 | H | S | 3 | C(O)NH | 4 | NHC(O)O | CH2C6H5 | O | OCH3 | |
| 68 | 4-Pyridinyl | o-CH3C6H4 | H | S | 3 | C(O)NH | 4 | NHC(O)O | CH2C6H5 | O | OCH3 | |

*All nmr data are in the Experimental Text (see above).
Footnote: sb = single bond, db = double bond

Utility

The compounds of the present invention are inhibitors of the enzyme acyl-CoA: cholesterol acyltransferase and are thus effective in inhibiting esterification and transport of cholesterol across the intestinal wall. In addition, the compounds are useful in preventing the formation of cholesterol ester rich macrophages (foam cells) in the arterial wall through the inhibition of cholesterol ester formation. Foam cells are a source of the large quantity of cholesterol ester found in atheromatous lesions as opposed to the surrounding undiseased tissue. Thus inhibition of ACAT would decrease the accumulation and storage of cholesterol esters in the arterial wall and prevent or inhibit the formation of atheromatous lesions.

A. Assay of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mls of Dulbecco's Eagle Medium (DMEM) supplemented with 10% fetal bovine serum (FBS). Cells were incubated at 37° C. in an atmosphere of 5% $CO_2$ and 93% humidity. After 24 hours the media was changed to 0.68 mls 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μl/ml maximum). At 43 hours, the cells were pulsed with 0.1 mM $^{14}C$-oleic acid (10,000 dpm/nmol) complexed with BSA (bovine serum albumin) to follow cholesterol ester formation. The experiment was terminated at 45 hours by washing the monolayers 3 time with 3 ml of Tris-buffered saline at 4° C. The lipids were extracted by incubating the monolayers with 1.5 ml of hexane: isopropanol (3:2, v/v) for 30 min. under gentle agitation. During this period, 10,000 dpm $^3H$-cholesteryl linoleate and 10 μg of cholesteryl oleate were added as an internal standard and carrier respectively. The organic solvent was removed and the cells were washed with an additional 1.0 ml of hexane: isopropanol which was combined with the original extract. The cells were allowed to dry overnight, digested with 1.5 ml of 0.2N sodium hydroxide for 1 hour and an aliquot of the solubilized protein used for protein determination using the Lowry method. The organic extract was taken to dryness, the residue resuspended in 100 μl of chloroform and the lipids separated on silica gel impregnated glass fiber plates using a hexane: diethylether: acetic acid (170:30:1, v/v/v) solvent system. Individual lipids were visualized with iodine and the cholesteryl ester spot cut out and transferred to scintillation vials to determine the amount of radioactivity. The conversion of oleic acid to cholesteryl ester in the control averaged 0.54 mmol/hour/mg protein and was increased upon the addition of ac-LDL to about 10.69±0.69 mmol/hour/mg protein. The inhibition of esterification by the compounds is shown in Table 2; the data are expressed as the concentration at which ACAT activity is inhibited by 50% ($IC_{50}$).

TABLE 2

Inhibition of Cholesterol of Esterification in Macrophage by Various Compounds

| Compound of Example | Cholesterol Esterification $IC_{50}$ (nM) |
|---|---|
| 1 | 37 |
| 2 | 100,000 |
| 3 | 386 |
| 4 | 601 |
| 5 | 7150 |
| 6 | 10,330 |
| 7 | 1,100 |
| 8 | 4.9 |
| 9 | 650 |
| 10 | 4620 |
| 11 | 13,400 |

Dosage Forms

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*, 16th Edition, 1980.

In their therapeutic use as antihypercholesterolemic and/or antiatherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets

Tablets are prepared by conventional procedures so that the dosage unit is 500 milligrams of active ingredient, 150 milligrams of lactose, 50 milligrams of cellulose and 10 milligrams of magnesium stearate.

Capsules

Capsules are prepared by conventional procedures so that the dosage unit is 500 milligrams of active ingredient, 100 milligrams of cellulose and 10 milligrams of magnesium stearate.

| Syrup | |
|---|---|
|  | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | Wt. % |
| --- | --- |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendible Powder | Wt. % |
| --- | --- |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | Wt. % |
| --- | --- |
| Active Ingredient | 10 |
| Sodium Saccharin | 0.02 |
| Gelatin | 2 |
| Colorant, Flavor and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | Wt. % |
| --- | --- |
| Active Ingredient | 10 |
| Gelcarin ® (Carrageenin gum) | 1 |
| Sodium Saccharin | 0.01 |
| Colorant, Flavor and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | Wt. % |
| --- | --- |
| Active Ingredient | 30 |

| Emulsifiable Paste | Wt. % |
| --- | --- |
| Tween ® 80 and Span ® 80 | 6 |
| Keltrol ® | 0.5 |
| Mineral Oil | 63.5 |

All the ingredients are carefully mixed together to make a homogeneous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited publications and applications may provide further useful information, however, these cited materials are hereby incorporated by reference.

What is claimed is:

1. A compound of the Formula (I) or Formula (1a) when Q is a double bond:

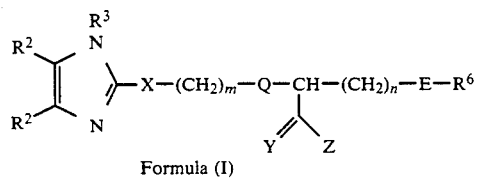

Formula (I)

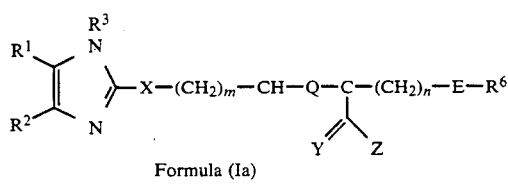

Formula (Ia)

when Q is a double bond the stereoisomers or pharmaceutically acceptable salts thereof, wherein:

$R^1$ and $R^2$ are independently selected from H, $C_1$–$C_8$ branched alkyl, $C_3$–$C_{10}$ cycloalkyl, $C_4$–$C_{10}$ cycloalkylalkyl, $C_7$–$C_{14}$ arylalkyl, 2-, 3-, or 4-pyridinyl, 2-thienyl, 2-furanyl, phenyl or phenyl substituted with 1 to 3 substituents each of which is independently selected from F, Cl, Br, OH, CN, $C_1$–$C_4$ alkoxy, $C_1$–$C_4$ alkyl, $C_3$–$C_8$ branched alkyl, $CH_3S(O)_r$, $NO_2$, $CF_3$, $NR^7R^8$ or $NR^7C(O)R^8$;

$R^3$ is, $C_1$–$C_6$ alkyl, allyl, or benzyl or phenyl or benzyl or phenyl substituted with F, Cl, $CH_3$, $CH_3O$, or $CF_3$; or $C_1$–$C_4$ carboalkyl;

$R^4$ is H, straight chain $C_1$–$C_8$, $C_3$–$C_8$ branched alkyl, $C_3$–$C_7$ cycloalkyl, $C_4$–$C_{10}$ cycloalkylalkyl, $C_1$–$C_3$ perfluoroalkyl, or benzyl or phenyl or benzyl or phenyl substituted with 1 to 3 substituents each of which is independently selected from $C_1$–$C_4$ alkyl, $C_3$–$C_8$ branched alkyl, $C_1$–$C_4$ alkoxy, F, Br, Cl, $NH_2$, OH, CN, $CO_2H$, $CF_3$, $NO_2$, $C_1$–$C_4$ carboalkoxy, $NR^7R^8$ or $NR^7C(O)R^8$; 2-, 3-, or 4-pyridinyl, pyrimidinyl or biphenyl;

$R^5$ is H, $C_1$–$C_6$ alkyl or benzyl;

$R^6$ is H, $C_1$–$C_8$ alkyl, $C_3$–$C_8$ branched alkyl, $C_3$–$C_7$ cycloalkyl, $C_4$–$C_{10}$ cycloalkylalkyl, or, benzyl or phenyl or benzyl or phenyl substituted with 1 to 3 substituents each of which is independently selected from $C_1$–$C_4$ alkyl or alkoxy, F, Br, Cl, $NH_2$, OH, CN, $CO_2H$, $CF_3$, $NO_2$, $C_1$–$C_3$ carboalkoxy, $NR^7R^8$, or $NR^7C(O)R^8$; or pentafluorophenyl;

$R^7$ and $R^8$ are independently selected from H, or $C_1$–$C_4$ alkyl, benzyl or phenyl;

X is $S(O)_r$, O, $NR^5$, or a single bond;

Y is O, S, $H_2$, or $NR^7$;

Z is $NHR^4$, $OR^4$ or $R^4$; provided that when Y—$NR^7$, Z cannot be $OR^4$ or $R^4$;

m and n are 1–6;

r is 0–2;

Q is selected from a double bond, —C(O)N(R7)—, —N(R7)C(O)—, —C(O)O—, or —OC(O)—

E is selected from O, $NR^7$, S, —C(O)N($R^7$)—, —N($R^7$)C(O)—, —N($R^7$)C(O)N($R^8$)—, —N($R^7$)C(O)O—, —OC(O)N($R^7$)—, —N($R^7$)C(NH)N($R^8$)—, —C(O)0—, or —OC(O)—.

2. A compound of claim 1 wherein:

$R^1$ and $R^2$ are independently selected from $C_1$–$C_8$ alkyl, $C_3$–$C_8$ branched alkyl, $C_3$–$C_{10}$ cycloalkyl, $C_4$–$C_{10}$ cycloalkylalkyl, $C_7$–$C_{14}$ arylalkyl, 2-, 3-, or 4- pyridinyl, 2-thienyl, 2-furanyl, phenyl or phenyl substituted with 1 to 2 substituents each of which is independently selected from F, Cl, Br, OH, CN, $C_1$–$C_4$ alkoxy, $C_1$–$C_4$ alkyl, $C_3$–$C_8$ branched alkyl, $CH_3S(O)_r$, $NO_2$, $CF_3$, $NR^7R^8$ or $NR^7C(O)R^8$;

$R^3$ is H, $C_1$–$C_6$ alkyl, allyl, benzyl or phenyl, $C_1$–$C_4$ carboalkyl;

$R^4$ is straight chain $C_1$–$C_8$, $C_3$–$C_8$ branched alkyl, $C_3$–$C_7$ cycloalkyl, $C_4$–$C_{10}$ cycloalkylalkyl, $C_1$–$C_3$ perfluoroalkyl, or, benzyl or phenyl or benzyl or phenyl substituted with 1 to 3 substituents each of which is independently selected from $C_1$–$C_4$ alkyl, $C_3$–$C_8$ branched alkyl, $C_1$–$C_4$ alkoxy, F, Br, Cl, $NH_2$, OH, CN, $CO_2H$, $CF_3$, $NO_2$, $C_1$–$C_4$ carboalkoxy, $NR^7R^8$ or $NR^7C(O)R^8$; 2-, 3-, or 4- pyridinyl, pyrimidinyl or biphenyl;

$R^6$ is $C_1$–$C_8$ alkyl, $C_3$–$C_8$ branched alkyl, $C_3$–$C_7$ cycloalkyl, $C_4$–$C_{10}$ cycloalkyl, or, benzyl or phenyl or benzyl or phenyl substituted with 1 to 2 substituents each of which is independently selected from C1–C4 alkyl or alkoxy, F, Br, Cl, $NH_2$, OH, CN, $CO_2H$, $CF_3$, $NO_2$, $C_1$–$C_3$ carboalkoxy, $NR^7R^8$, or $NR^7C(O)R^8$; or pentafluorophenyl;

$R^7$ and $R^8$ are independently selected from H, or C1–C4 alkyl;

X is $S(O)_r$ or a single bond; and

Y is O, S, or $H_2$.

3. A compound of claim 2 wherein:

$R^1$ and $R^2$ are independently selected from $C_1$–$C_8$ alkyl, $C_3$–$C_8$ branched alkyl, $C_3$–$C_{10}$ cycloalkyl, $C_4$–$C_{10}$ cycloalkylalkyl, $C_7$–$C_{14}$ arylalkyl, 2-, 3-, or 4- pyridinyl, 2-thienyl, 2-furanyl, phenyl or phenyl substituted with 1 to 2 substituents each of which is independently selected from F, Cl, Br, OH, CN, $C_1$–$C_4$ alkoxy, $C_1$–$C_4$ alkyl, $C_3$–$C_8$ branched alkyl, $CH_3S(O)_r$, $NO_2$, $CF_3$, or $NR^7R^8$ where $R^7$ and $R^8$ are $C_1$–$C_4$ alkyl;

$R^3$ is H, or $C_1$–$C_4$ carboalkyl;

$R^4$ is straight chain $C_1$–$C_8$, $C_3$–$C_8$ branched alkyl, $C_3$–$C_7$ cycloalkyl, or, benzyl or phenyl or benzyl or phenyl substituted with 1 to 2 substituents each of which is independently selected from $C_1$–$C_4$ alkyl, $C_3$–$C_6$ branched alkyl, $C_1$–$C_4$ alkoxy, F, Br, Cl, CN, $CF_3$, $NO_2$, or $C_1$–$C_4$ carboalkoxy;

$R^6$ is $C_1$–$C_8$ alkyl, $C_3$–$C_8$ branched alkyl, $C_3$–$C_7$ cycloalkyl, $C_4$–$C_{10}$ cycloalkylalkyl, or, benzyl or phenyl or benzyl or phenyl substituted with 1 to 2 substituents each of which is independently selected from $C_1$–$C_4$ alkyl or alkoxy, F, Cl, OH, CN, $CF_3$, $NO_2$, or $C_1$–$C_3$ carboalkoxy;

$R^7$ and $R^8$ are H;

X is $S(O)_r$; and

Y is O, $H_2$.

4. A compound selected from the group consisting essentially of:

N2-[4-[4,5-bis(4-methoxyphenyl)-1H-imidazol-2-yl[thio]-1-oxobutyl]-N6-[(phenylmethoxy)carbonyl]-L-lysine, methyl ester, N6-(1-adamantylcarbonyl)-N2-[4-[4,5-bis(4-methoxyphenyl)-1H-imidazol-2-yl[thio]-1-oxobutyl], methyl ester, N2-[4-[4,5-bis(4-methoxyphenyl)-1H-imidazol-2-yl[thio]-1-oxobutyl]-N6-[(phenylmethyl)-aminocarbonyl]-L-lysine, methyl ester, N6-acetyl-N2-[4-[1-acetyl-4,5-bis(4-methoxyphenyl)-1H-imidazol-2-yl[thio]--oxobutyl]-L-lysine, methyl ester, N6-acetyl-N2-[4-[4,5-bis(4-methoxyphenyl)-1H-imidazol-2-yl[thio]-1-oxobutyl]-L-lysine, methyl ester, phenylmethyl, (S)-[5-[[4-[4,5-bis(4-methoxyphenyl)-1H-imidazol-2-yl[thio]-1-oxobutyl]amino]-6-[(1-methylethyl)amino]-6-oxohexyl]carbamate and, N2-[4-[4,5-bis[4-(dimethylamino)phenyl]-1H-imidazol-2-ylthio]-1-oxobutyl]-N6-[(phenylmethoxy)carbonyl]-L-lysine, methyl ester], N-[4-[4,5-bis(4-methoxyphenyl)-1H-imidazol-2-yl[thio]-1-oxobutyl]-norieucine, methyl ester, ethyl, 7-(4,5-diphenyl-1H-imidazol-2-ylthio)-2-heptenate, 7-(4,5-diphenyl-1H-imidazol-2-ylthio)-2-heptenoic acid, and N-(2,4-difluorophenyl)-7-(4,5-diphenyl-1H-imidazol-2-ylthio-2-pentyl-2-heptenamide)].

5. The compound of claim 4 which is N2-[4-[4,5-bis(4-methoxyphenyl)-1H-imidazol-2-ylthio]-1-oxobutyl]-N6-[(phenylmethoxy)carbonyl]-L-lysine, methyl ester.

6. The compound of claim 4 which is N2-[4-[4,5-bis[4-(dimethylamino)phenyl]-1H-imidazol-2-ylthio]-1-oxobutyl]-N6-[(phenylmethoxy)carbonyl]-L-lysine, methyl ester.

7. The compound of claim 4 which is N6-(1-adamantylcarbonyl)2-[4-[4,5-bis(4-methoxyphenyl)-1H-imidazol-2-ylthio]-1-oxobutyl]-L-lysine, methyl ester.

8. The compound of claim 4 which is N2-[4-[4,5-bis(4-methoxyphenyl)-1H-imidazol-2-ylthio]-1-oxobutyl]-N6-[(phenylmethyl)aminocarbonyl]-L-lysine, methyl ester.

9. The compound of claim 4 which is N2-[4-[4,5-bis(4-methoxyphenyl)-1H-imidazol-2-ylthio]-1-oxobutyl]-N6-[(phenylmethoxy)carbonyl]-L-lysine, methyl ester.

10. The compound of claim 4 which is N2-[4-[4,5-bis[4-(dimethylamino)phenyl]-1H-imidazol-2-ylthio]-1-oxobutyl]-N6-[(phenylmethoxy)carbonyl]-L-lysine, methyl ester.

11. The compound of claim 4 which is N6-(1-adamantylcarbonyl)-N2-[4-[4,5-bis(4-methoxyphenyl)-1H-imidazol-2-ylthio]-1-oxobutyl]-L-lysine, methyl ester.

12. The compound of claim 4 which is N2-[4-[4,5-bis(4-methoxyphenyl)-1H-imidazol-2-ylthio]-1- oxobutyl]-N6-[(phenylmethyl)aminocarbonyl]-L-lysine, methyl ester.

13. A pharmaceutical composition comprising an effective ACAT inhibiting or antiatherosclerotic amount of a compound of the formula (I):

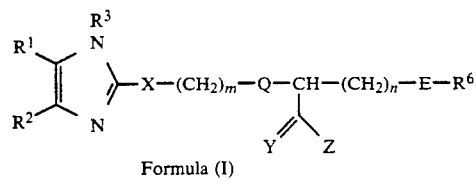

Formula (I)

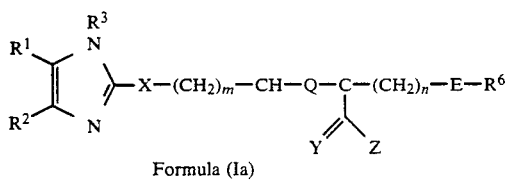

Formula (Ia)

when Q is a double bond the stereoisomers or pharmaceutically acceptable salts thereof, wherein:

$R^1$ and $R^2$ are independently selected from H, $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4- pyridinyl, 2-thienyl, 2-furanyl, phenyl or phenyl substituted with 1 to 3 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is H, $C_1$-$C_6$ alkyl, allyl, or benzyl or phenyl or benzyl or phenyl substituted with F, Cl, $CH_3$, $CH_3O$, or $CF_3$; or $C_1$-$C_4$ carboalkyl;

$R^4$ is H, straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl or, benzyl or phenyl or benzyl or phenyl substituted with 1 to 3 substituents each of which is independently selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4- pyridinyl, pyrimidinyl or biphenyl;

$R^5$ is H, $C_1$-$C_8$ alkyl or benzyl;

$R^6$ is H, $C_1$-$C_8$ alkyl, $C_3$-$C_8$ branched alkyl, $C_3$-$C_7$ cycloalkyl, $C_4$-$C_{10}$ cycloalkyl, or, benzyl or phenyl or benzyl or phenyl substituted with 1 to 3 substituents each of which is independently selected from $C_1$-$C_4$ alkyl or alkoxy, F, Br, Cl, $NH_2$, OH, CN, $CO_2H$, $CF_3$, $NO_2$, $C_1$-$C_3$ carboalkoxy, $NR^7R^8$, or $NR^7C(O)R^8$; or pentafluoro-phenyl;

$R^7$ and $R^8$ are independently selected from H, or $C_1$-$C_4$ alkyl, benzyl or phenyl;

X is $S(O)_r$, O, $NR^5$, or a single bond;

Y is O, S, $H_2$, or $NR^7$;

Z is $NHR^4$, $OR^4$ or $R^4$; provided that when Y=$NR^7$, Z cannot be $OR^4$ or $R^4$;

m and n are 1-6;

r is 0-2;

Q is selected from a double bond, —C(O)N(R7)—, —N(R7)C(O)—, —C(O)O—, or —OC(O)—;

E is selected from O, $NR^7$, S, —C(O)N(R7)—, —N(R7)C(O)—, —N(R7)C(O)N(R8)—, —N(R7)C(O))—, —OC(O)N(R7)—, —N(R7)C(NH)N(R8)—, —C(O)O—, or —OC(O)—.

14. A pharmaceutical composition of claim 13 wherein:

$R^1$ and $R^2$ are independently selected from $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl or phenyl substituted with 1 to 2 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is H, $C_1$-$C_6$ alkyl, allyl, benzyl or phenyl, $C_1$-$C_4$ carboalkyl;

$R^4$ is straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl, or, benzyl or phenyl or benzyl or phenyl substituted with 1 to 3 substituents each of which is independently selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4-pyridinyl, pyrimidinyl or biphenyl;

$R^6$ is $C_1$-$C_8$ alkyl, $C_3$-$C_8$ branched alkyl, $C_3$-$C_7$ cycloalkyl, $C_4$-$C_{10}$ cycloalkylalkyl, or, benzyl or phenyl or benzyl or phenyl substituted with 1 to 2 substituents each of which is independently selected from $C_1$-$C_4$ alkyl or alkoxy, F, Br, Cl, $NH_2$, OH, CN, $CO_2H$, $CF_3$, $NO_2$, $C_1$-$C_3$ carboalkoxy, $NR^7R^8$, or $NR^7C(O)R^8$; or pentafluorophenyl;

$R^7$ and $R^8$ are independently selected from H, or $C_1$-$C_4$ alkyl;

X is $S(O)_r$ or a single bond; and

Y is O, S, or $H_2$.

15. A pharmaceutical composition of claim 14 wherein:

$R^1$ and $R^2$ are independently selected from $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl or phenyl substituted with 1 to 2 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$ where $R^7$ and $R^8$ are $C_1$-$C_4$ alkyl;

$R^3$ is H, or $C_1$-$C_4$ carboalkyl;

$R^4$ is straight chain $C_1$-$C_8$, $C_3$-$C_8$ branched alkyl, $C_3$-$C_7$ cycloalkyl, $C_4$-$C_{10}$ cycloalkylalkyl, or benzyl or phenyl or benzyl or phenyl substituted with 1 to 2 substituents each of which is independently selected from $C_1$-$C_4$ alkyl, $C_3$-$C_6$ branched alkyl, $C_1$-$C_4$ alkoxy, F, Br, Cl, CN, $CF_3$, $NO_2$, or $C_1$-$C_4$ carboalkoxy;

$R^6$ is $C_1$-$C_8$ alkyl, $C_3$-$C_8$ branched alkyl, $C_3$-$C_7$ cycloalkyl, $C_4$-$C_{10}$ cycloalkylalkyl, or, benzyl or phenyl or benzyl or phenyl substituted with 1 to 2 substituents each of which is independently selected from $C_1$-$C_4$ alkyl or alkoxy, F, Cl, OH, CN, $CF_3$, $NO_2$, or $C_1$-$C_3$ carboalkoxy;

$R^7$ and $R^8$ are H;

X is $S(O)_r$; and

Y is O, $H_2$.

16. A pharmaceutical composition of claim 15 wherein the compound is selected from the group consisting essentially of N2-[4-[4,5-bis(4-methoxyphenyl)-1H-imidazol-2-ylthio]-1-oxobutyl]-N6-[(phenylmethoxy)carbonyl]-L-lysine, methyl ester, N6-(1-adamantylcarbonyl)-N2-[4-[4,5-bis(4-methoxyphenyl)-1H-imidazol-2-ylthio]-1-oxobutyl]-L-lysine, methyl ester, N2-[4-[4,5-bis(4-methoxyphenyl)-1H-imidazol-2-ylthio]-1-oxobutyl]-N6-[(phenylmethyl)-aminocarbonyl]-L-lysine, methyl ester, N6-acetyl-N2-[4-[1-acetyl-4,5-bis(4-methoxyphenyl)-1H-imidazol-2-ylthio]-1-oxobutyl]-L-lysine, methyl ester, N6-acetyl-N2-[4-[4,5-bis(4-methoxyphenyl)-1H-imidazol-2-ylthio]-1-oxobutyl]-L-lysine, methyl ester, phenylmethyl, (S)-[5-[[4-[4,5-bis(4-methoxyphenyl)-1H-imidazol-2-ylthio]-1-oxobutyl]amino]-6-[(1methylethyl)amino]-6-oxohexyl]carbamate, and N2-[4-[4,5-bis[4-(dimethylamino)phenyl]-1H-imidazol-2-ylthio]-1-oxobutyl]-N6-[(phenylmethoxy)carbonyl]-L-lysine, methyl ester.

17. A pharmaceutical composition of claim 16 wherein the compound of N2-[4-[4,5-bis(4-methoxyphenyl)-1H-imidazol-2-ylthio]-1-oxobutyl]-N6-[(phenylmethoxy)-carbonyl]-L-lysine, methyl ester.

18. A pharmaceutical composition of claim 16 wherein the compound of N2-[4-[4,5-bis[4-(dimethylamino)phenyl]-1H-imidazol-2-ylthio]-1-oxobutyl]-N6-[(phenylmethoxy)carbonyl]-L-lysine, methyl ester.

19. A pharmaceutical composition of claim 16 wherein the compound of N6-(1-adamantylcarbonyl)-N2-[4-[4,5-bis(4-methoxyphenyl)-1H-imidazol-2-ylthio]-1-oxobutyl]-L-lysine, methyl ester.

20. A pharmaceutical composition of claim 16 wherein the compound of N2-[4-[4,5-bis(4-methoxyphenyl)-1H-imidazol-2-ylthio]-1-oxobutyl]-N6-[(phenylmethyl)aminocarbonyl]-L-lysine, methyl ester.

21. A method of treating hypercholesterolemia or atherosclerosis in a mammal, said method comprising administering to a mammal in need of such treatment a therapeutically effective amount of a compound of the formula (I):

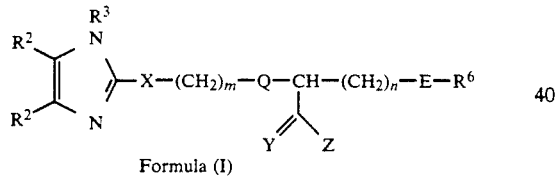

Formula (I)

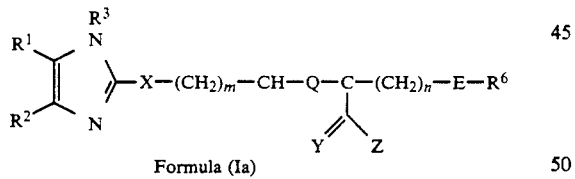

Formula (Ia)

when Q is a double bond the stereoisomers or pharmaceutically acceptable salts thereof, wherein:

$R^1$ and $R^2$ are independently selected from H, $C_1$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl or phenyl substituted with 1 to 3 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is, $C_1$-$C_6$ alkyl, allyl, or benzyl or phenyl or benzyl or phenyl substituted with F, Cl, $CH_3$, $CH_3O$, or $CF_3$; or $C_1$-$C_4$ carboalkyl;

$R^4$ is H, straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl, or benzyl or phenyl or benzyl or phenyl substituted with 1 to 3 substituents each of which is independently selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4-pyridinyl, pyrimidinyl or biphenyl;

$R^5$ is H, $C_1$-$C_6$ alkyl or benzyl;

$R^6$ is H, $C_1$-$C_8$ alkyl, $C_3$-$C_8$ branched alkyl, $C_3$-$C_7$ cycloalkyl, $C_4$-$C_{10}$ cycloalkylalkyl, or, benzyl or phenyl or benzyl or phenyl substituted with 1 to 3 substituents each of which is independently selected from $C_1$-$C_4$ alkyl or alkoxy, F, Br, Cl, $NH_2$, OH, CN, $CO_2H$, $CF_3$, $NO_2$, $C_1$-$C_3$ carboalkoxy, $NR^7R^8$, or $NR^7C(O)R^8$; or pentafluorophenyl;

$R^7$ and $R^8$ are independently selected from H, or $C_1$-$C_4$ alkyl, benzyl or phenyl;

X is $S(O)_r$, O, $NR^5$, or a single bond;

Y is O, S, $H_2$, or $NR^7$;

Z is $NHR^4$, $OR^4$ or $R^4$; provided that when Y=$NR^7$, Z cannot be $OR^4$ or $R^4$;

m and n are 1-6;

r is 0-2;

Q is selected from a double bond, —C(O)N(R7)—, —N(R7)C(O)—, —C(O)O—, or —OC(O)—;

E is selected from O, $NR^7$, S, —C(O)N(R7)—, —N(R7)C(O)—, —N(R7)C(O)N(R8)—, —N(R7)C(O)O—, —OC(O)N(R7)—, —N(R7)C(NH)N(R8)—, —C(O)O—, or —OC(O)—.

22. The method of claim 21 wherein:

$R^1$ and $R^2$ are independently selected from $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, or 4-pyridinyl, 2-thienyl, 2-furanyl, phenyl or phenyl substituted with 1 to 2 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, $NR^7R^8$ or $NR^7C(O)R^8$;

$R^3$ is H, $C_1$-$C_6$ alkyl, allyl, benzyl or phenyl, $C_1$-$C_4$ carboalkyl;

$R^4$ is straight chain $C_1$-$C_8$, $C_3$-$C_8$ branched alkyl, $C_3$-$C_7$ cycloalkyl, $C_4$-$C_{10}$ cycloalkylalkyl, $C_1$-$C_3$ perfluoroalkyl, benzyl or phenyl or benzyl or phenyl substituted with 1 to 3 substituents each of which is independently selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NR^7C(O)R^8$; 2-, 3-, or 4-pyridinyl, pyrimidinyl or biphenyl;

$R^6$ is $C_1$-$C_8$ alkyl, $C_3$-$C_8$ branched alkyl, $C_3$-$C_7$ cycloalkyl, $C_4$-$C_{10}$ cycloalkylalkyl, or, benzyl or phenyl or benzyl or phenyl substituted with 1 to 2 substituents each of which is independently selected from $C_1$-$C_4$ alkyl or alkoxy, F, Br, Cl, $NH_2$ OH, CN, $CO_2H$, $CF_3$, $NO_2$, $C_1$-$C_3$ carboalkoxy, $NR^7R^8$, or $NR^7C(O)R^8$; or pentafluorophenyl;

$R^7$ and $R^8$ are independently selected from H, or $C_1$-$C_4$ alkyl;

X is $S(O)_r$ or a single bond; and

Y is O, S, or $H_2$.

23. The method of claim 22 wherein:

$R^1$ and $R^2$ are independently selected from $C_1$-$C_8$ alkyl, $C_3$-$C_8$ branched alkyl, $C_3$-$C_{10}$ cycloalkyl, $C_4$-$C_{10}$ cycloalkylalkyl, $C_7$-$C_{14}$ arylalkyl, 2-, 3-, 4-pyridinyl, 2-thienyl, 2-furanyl, phenyl or phenyl substituted with 1 to 2 substituents each of which is independently selected from F, Cl, Br, OH, CN, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$ where $R^7$ and $R^8$ are $C_1$–$C_4$ alkyl;

$R^3$ is H, or $C_1$–$C_4$ carboalkyl;

$R^4$ is straight chain $C_1$–$C_8$, $C_3$–$C_8$ branched alkyl, $C_3$–$C_7$ cycloalkyl, $C_4$–$C_{10}$ cycloalkylalkyl, or benzyl or phenyl or benzyl or phenyl substituted with 1 to 2 substituents each of which is independently selected from $C_1$–$C_4$ alkoxy, F, Br, Cl, CN, $CF_3$, $NO_2$, or $C_1$–$C_4$ carboalkoxy;

$R^6$ is $C_1$–$C_8$ alkyl, $C_3$–$C_8$ branched alkyl, $C_3$–$C_7$ cycloalkyl, $C_4$–$C_{10}$ cycloalkylalkyl, or, benzyl or phenyl or benzyl or phenyl substituted with 1 to 2 substituents each of which is independently selected from $C_1$–$C_4$ alkyl or alkoxy, F, Cl, OH, CN, $CF_3$, $NO_2$, or $C_1$–$C_3$ carboalkoxy;

$R^7$ and $R^8$ are H;

X is $S(O)_r$; and

Y is O, $H_2$.

24. The method of claim 23 wherein the compound is selected from the group consisting essentially of:

N2-[4-[4,5-bis(4-methoxyphenyl)-1H-imidazol-2-ylthio]-1-oxobutyl]-N6-[(phenylmethoxy)carbonyl]-L-lysine, methyl ester, N6-(1-adamantycarbonyl)-N2-[4-[4,5-bis(4-methoxyphenyl)-1H-imidazol-2-ylthio]-1-oxobutyl]-L-lysine, methyl ester, N2-[4-[4,5-bis(4-methoxyphenyl)-1H-imidazol-2-ylthio]-1-oxobutyl]-N6-[(phenylmethyl)-aminocarbonyl]-L-lysine, methyl ester, N6-acetyl-N2-[4-[1-acetyl-4,5-bis(4-methoxyphenyl)-1H-imidazole-2-ylthio]-1-oxobutyl]-L-lysine, methyl ester, N6-acetyl-N2-[4-[4,5-bis(4-methoxyphenyl)-1H-imidazole-2-ylthio]-1-oxobutyl]-L-lysine, methyl ester, phenylmethyl, (S)-[5-[[4-[4,5-bis(4-methoxyphenyl)-1H-imidazol-2-ylthio]-1-oxobutyl]amino]-6-[(1-methylethyl)amino]-6-oxohexyl]carbamate, and N2-[4[4,5-bis[4-(dimethylamino)phenyl]-1H-imidazol-2-ylthio]-1-oxobutyl]-N6-[(phenylmethoxy)carbonyl]-L-lysine, methyl ester.

* * * * *